(12) United States Patent
Seike et al.

(10) Patent No.: US 9,157,884 B2
(45) Date of Patent: Oct. 13, 2015

(54) METHOD FOR ELECTROCHEMICALLY DETECTING TARGET SUBSTANCE, METHOD FOR ELECTROCHEMICALLY DETECTING ANALYTE, AND DETECTION SET

(75) Inventors: Masayoshi Seike, Kobe (JP); Nobuyasu Hori, Kobe (JP); Seigo Suzuki, Kobe (JP); Shigeki Iwanaga, Kobe (JP); Hiroya Kirimura, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 600 days.

(21) Appl. No.: 13/218,113

(22) Filed: Aug. 25, 2011

(65) Prior Publication Data
US 2012/0048747 A1 Mar. 1, 2012

(30) Foreign Application Priority Data

Aug. 27, 2010 (JP) .................................. 2010-191398
Aug. 15, 2011 (JP) .................................. 2011-177514

(51) Int. Cl.
*G01N 27/26* (2006.01)
*G01N 27/327* (2006.01)
*G01N 27/74* (2006.01)

(52) U.S. Cl.
CPC .......... *G01N 27/3278* (2013.01); *G01N 27/745* (2013.01)

(58) Field of Classification Search
CPC ................ G01N 27/3275–27/3276; G01N 33/531–33/535; G01N 33/58–33/60; G01N 33/53; G01N 33/5302; G01N 33/5306; G01N 33/536–33/556
USPC .......... 435/287.1–288.7, 6.1–6.19; 205/777.5
See application file for complete search history.

(56) References Cited

U.S. PATENT DOCUMENTS

| | | | |
|---|---|---|---|
| 4,293,310 A * | 10/1981 | Weber | 436/536 |
| 5,776,672 A | 7/1998 | Hashimoto et al. | |
| 5,972,692 A | 10/1999 | Hashimoto et al. | |
| 2003/0022150 A1 * | 1/2003 | Sampson et al. | 435/4 |
| 2005/0069932 A1 * | 3/2005 | Arinaga et al. | 435/6 |
| 2009/0294305 A1 | 12/2009 | Bekki et al. | |
| 2010/0184028 A1 * | 7/2010 | Hsing et al. | 435/6 |
| 2013/0344498 A1 * | 12/2013 | Marziali et al. | 435/6.12 |

FOREIGN PATENT DOCUMENTS

| | | |
|---|---|---|
| JP | 2009-68869 A | 4/2009 |
| JP | 2010-107345 A | 5/2010 |
| WO | 2007/116811 A1 | 10/2007 |

* cited by examiner

*Primary Examiner* — Gurpreet Kaur
(74) *Attorney, Agent, or Firm* — Sughrue Mion, PLLC

(57) ABSTRACT

In order to provide a method of electrochemically detecting a target substance, a method of electrochemically detecting an analyte, and a detection set which have a theoretical advantage in the measurement sensitivity obtained by a conventional electrochemical detection method using a working electrode with a trapping substance immobilized, can reuse the working electrode, and can detect an analyte regardless of the size thereof, there is provided a method including: attracting the target substance containing a labeling substance in a liquid sample to a working electrode in which a trapping substance for trapping the target substance containing a labeling substance is not present; and electrochemically detecting the target substance containing a labeling substance.

14 Claims, 18 Drawing Sheets

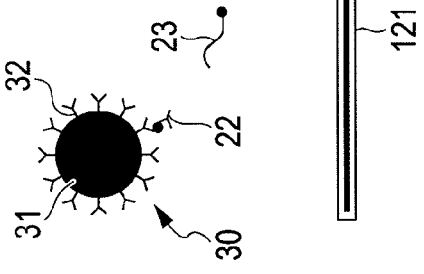
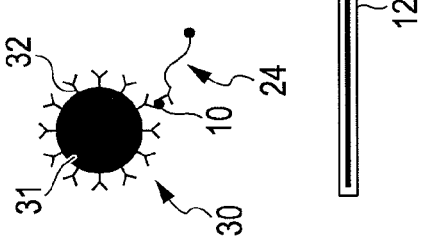
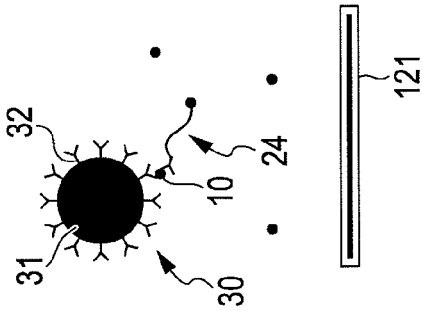
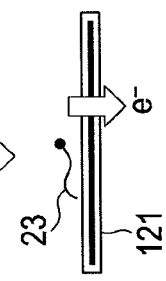
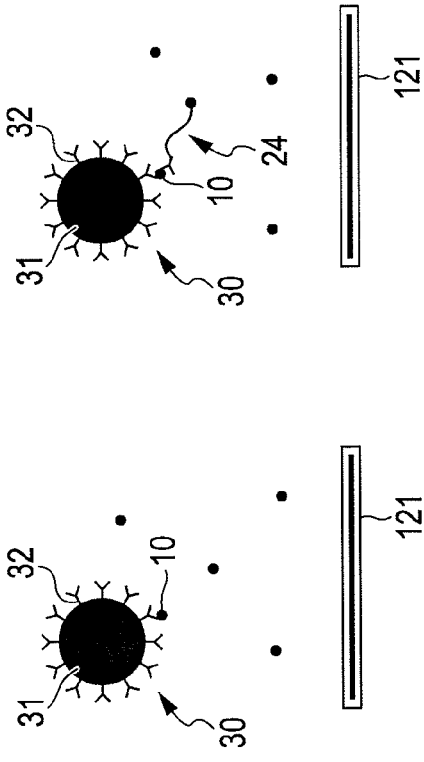
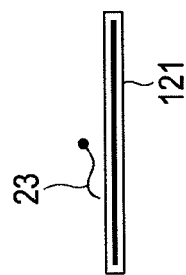

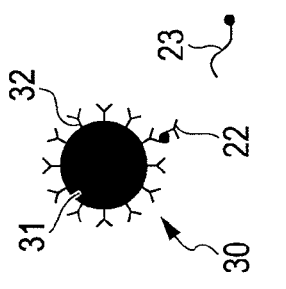 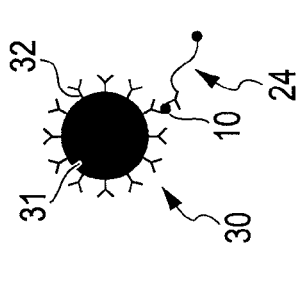 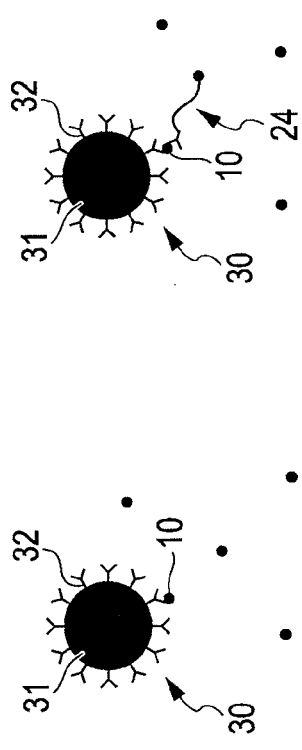
FIG. 14A  FIG. 14B  FIG. 14C  FIG. 14D
FIG. 14E  FIG. 14F

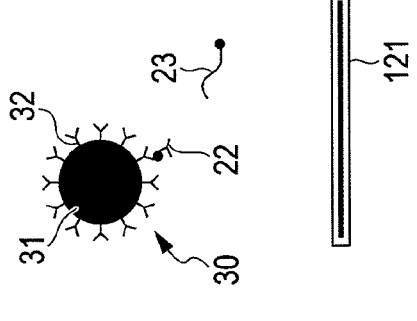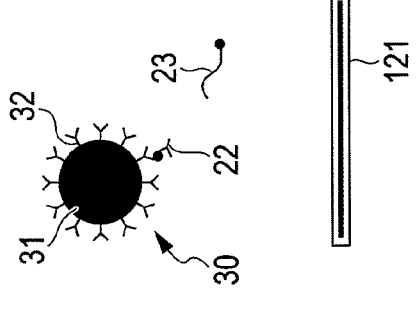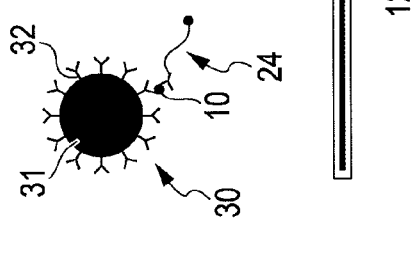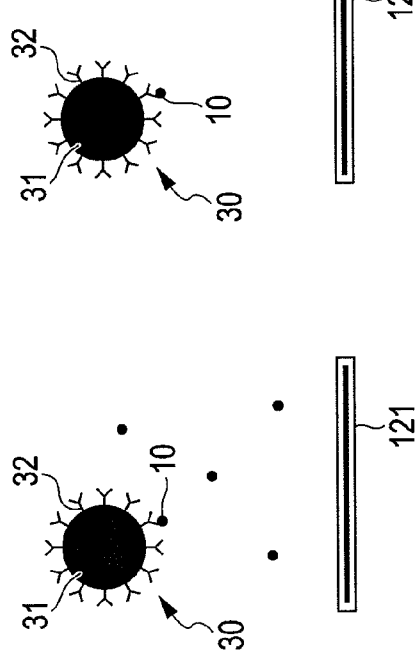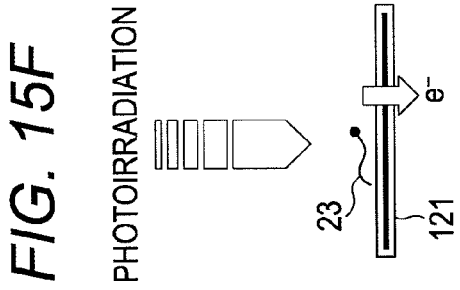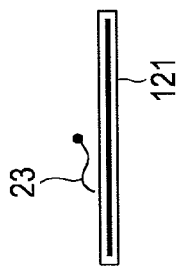

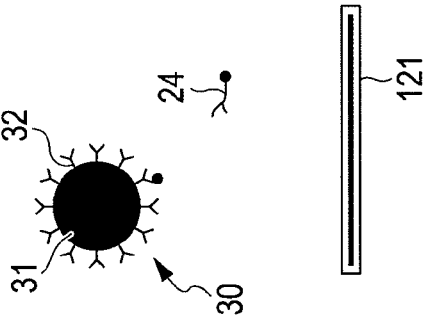
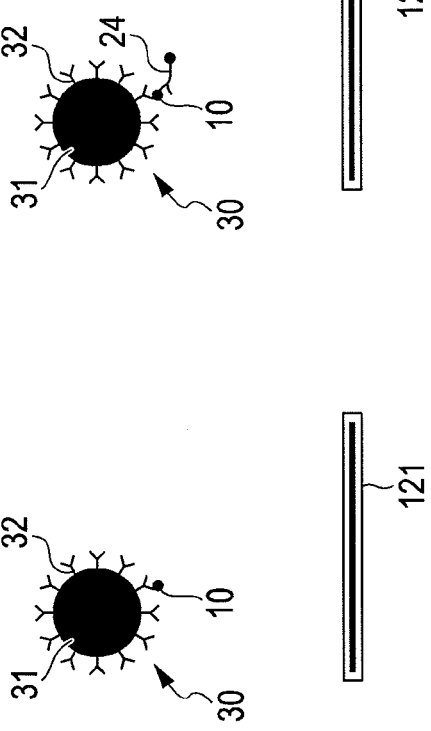
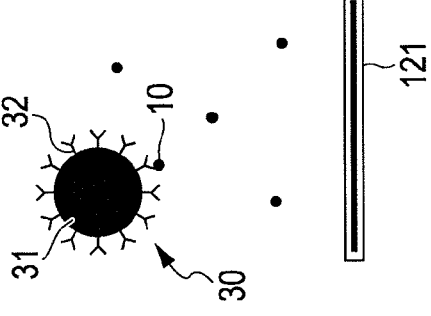
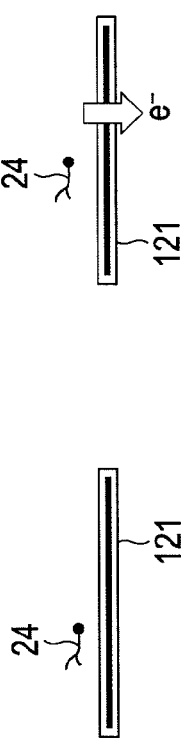

METHOD FOR ELECTROCHEMICALLY DETECTING TARGET SUBSTANCE, METHOD FOR ELECTROCHEMICALLY DETECTING ANALYTE, AND DETECTION SET

FIELD OF THE INVENTION

The present invention relates to a method of electrochemically detecting a target substance, a method of electrochemically detecting an analyte, and a detection set. More particularly, it relates to a method of electrochemically detecting a target substance, a method of electrochemically detecting an analyte, and a detection set which are useful for detecting and quantifying analytes such as nucleic acids and proteins as well as clinically examining and diagnosing diseases using these methods.

BACKGROUND

Clinical examination and diagnosis of diseases are performed by detecting genes and proteins related to the diseases which are contained in biological samples by detection methods such as a gene detection method and an immunological detection method. Examples of the detection methods include immunochromatography, latex agglutination, enzyme immunoassay, chemiluminescent immunoassay, and PCR assay.

On the other hand, a method of using an electric current generated by photoexcitation of a photochemically active labeling substance and light or an electric current generated by applying a voltage to an electrochemically active labeling substance to detect analytes such as genes and proteins is proposed for the purpose of improving detection sensitivity, quantitative performance, and simplicity (see, for example, U.S. Patent Publication No. 2009/294305, U.S. Pat. No. 5,776,672, and U.S. Pat. No. 5,972,692).

U.S. Patent Publication No. 2009/294305 describes a method of detecting an analyte, comprising: irradiating the analyte labeled with a photochemically active sensitizing dye with light; and measuring an electric current caused by photoexcitation of the sensitizing dye contained in the labeled analyte (hereinafter referred to as "photoelectrochemical detection"). In the method described in U.S. Patent Publication No. 2009/294305, the labeled analyte is brought into contact with a working electrode containing a trapping substance capable of binding directly or indirectly to the labeled analyte on the surface. Thus, the labeled analyte is immobilized on the working electrode through the trapping substance. Subsequently, the working electrode and a counter electrode are brought into contact with an electrolyte medium, and the labeled analyte immobilized on the working electrode is irradiated with light to excite the sensitizing dye. Thereafter, the analyte is specifically detected by measuring a photocurrent which flows between the working electrode and the counter electrode due to electronic transition from the photoexcited sensitizing dye to the working electrode.

U.S. Pat. No. 5,776,672 and U.S. Pat. No. 5,972,692 disclose gene detection methods using an electrode on which a single-stranded nucleic acid probe having a base sequence complementary to the gene to be detected is immobilized and a double-strand recognizing substance which specifically binds to double strand nucleic acid and contains a labeling substance which is electrochemically active. In the methods described in U.S. Pat. No. 5,776,672 and U.S. Pat. No. 5,972,692, a sample containing nucleic acid that is denatured into a single strand, a probe, the double-strand recognizing substance are contacted with one another. Then, a target gene is detected by measuring an oxidation reduction current and electrochemical luminescence based on the labeling substance contained in the double-strand recognizing substance bound to a double strand nucleic acid which is formed by hybridization between a nucleic acid corresponding to the target gene and a probe.

In these detection methods, the analyte is detected through a labeling substance that is electrochemically or photochemically active. Thus, the working electrode in which a trapping substance for trapping the analyte is immobilized on the surface so that the labeling substance is present near the working electrode depending on the amount of the analyte is used.

The working electrode in which a trapping substance is immobilized is hard to be reused. This is because, in order to reuse the working electrode with the trapping substance immobilized, it is necessary to remove substances other than the trapping substance on the working electrode by a cleaning process. However, the trapping substance may also be removed from the working electrode in the cleaning process. Further, the trapping substance on the working electrode may be denatured by a cleaning agent to be used in the cleaning process. Thus, the time of reusing the working electrode with the trapping substance immobilized may affect the measurement results. Therefore, a detection unit which includes the working electrode with the trapping substance immobilized is usually thrown away for each measurement process. Consequently, a detection system using the working electrode with the trapping substance immobilized has a disadvantage of higher costs per measurement.

As for the detection system using the working electrode with the trapping substance immobilized, when the analyte is large, it becomes difficult to allow the labeling substance to be present near the working electrode due to steric hindrance, resulting in reduced detection performance.

SUMMARY OF THE INVENTION

The scope of the present invention is defined solely by the appended claims, and is not affected to any degree by the statements within this summary.

The present invention has been achieved in view of the above circumstances. Its object is to provide a method of electrochemically detecting a target substance, a method of detecting an analyte, and a detection set which have a theoretical advantage in the measurement sensitivity obtained by a conventional electrochemical detection method using a working electrode with a trapping substance immobilized and can reuse the working electrode.

The present invention provides a method of electrochemically detecting a target substance, a method of detecting an analyte, and a detection set which are capable of detecting an analyte regardless of the size of the analyte.

In order to solve the above problems, the present inventors have conducted intensive examinations. As a result, they have found that a target substance containing a labeling substance is transported to near the surface of a working electrode using a specific liquid sample, thereby achieving electrochemical detection of the labeling substance, and the present invention has been completed.

A first aspect of the present invention is a method of electrochemically detecting a target substance containing a labeling substance, comprising:

attracting the target substance containing a labeling substance in a liquid sample to a working electrode in which a trapping substance for trapping the target substance containing a labeling substance is not present; and electrochemically detecting the target substance containing a labeling substance.

A second aspect of the present invention is a method of electrochemically detecting an analyte, comprising:

forming a complex containing a labeling substance and an analyte on a solid phase;

isolating the solid phase in which the complex is formed;

separating a target substance containing a labeling substance from the complex formed on solid phase which is obtained in the isolation process;

attracting the separated target substance containing a labeling substance to a working electrode in which a trapping substance for trapping the target substance containing a labeling substance is not present; and electrochemically detecting the target substance containing a labeling substance.

A third aspect of the present invention is a method of electrochemically detecting an electrochemically or photochemically active analyte, comprising:

immobilizing an analyte on a solid phase;

isolating the solid phase in which the analyte is immobilized;

separating the analyte or part of the analyte from the solid phase in which the analyte obtained in the isolation process is immobilized;

attracting the separated analyte or part of the analyte to a working electrode in which a trapping substance for trapping the analyte or part of the analyte is not present; and electrochemically detecting the analyte or the part of the analyte.

A fourth aspect of the present invention is a detection set for electrochemically detecting an analyte, comprising:

a solid phase in which a first trapping substance for trapping an analyte is immobilized;

a label binding substance containing a binding substance for trapping an analyte labeled with a labeling substance; and a test chip which includes a working electrode in which a second trapping substance for trapping a target substance containing a labeling substance which is separated from the binding substance is not present and a counter electrode composed of a conductive material.

According to the method of electrochemically detecting a target substance containing a labeling substance, the method of electrochemically detecting an analyte, and the detection set in the present invention, the target substance containing a labeling substance can be transported to near the working electrode. Thus, even if the trapping substance for trapping the target substance containing a labeling substance is not immobilized on the working electrode, the target substance containing a labeling substance or the analyte can be electrochemically detected. Therefore, the method of electrochemically detecting a target substance containing a labeling substance, the method of electrochemically detecting an analyte, and the detection set in the present invention have a theoretical advantage in the measurement sensitivity obtained by a conventional electrochemical detection method using a working electrode with a trapping substance immobilized.

Besides, the trapping substance which is damaged by a cleaning process is not present in the working electrode to be used, and thus the working electrode can be returned to a reusable state by a simple treatment. Therefore, the method of electrochemically detecting a target substance containing a labeling substance, the method of electrochemically detecting an analyte, and the detection set in the present invention produce an excellent effect such that the working electrode is reusable. As a result, the working electrode once used for the detection process is reusable. Accordingly, economical efficiency is improved and the clinical examination and diagnosis are achieved at low cost as compared to the conventional electrochemical detection method using a working electrode with a trapping substance immobilized.

In the method of electrochemically detecting an analyte and the detection set of the present invention according to the second to fourth aspects, the target substance containing a labeling substance is separated from the complex containing the labeling substance and the analyte formed on the solid phase. Then, the separated target substance containing a labeling substance is electrochemically detected using the working electrode in which the trapping substance is not present. Therefore, according to the method of electrochemically detecting an analyte and the detection set of the present invention, the analyte can be detected regardless of the size of the analyte.

BRIEF DESCRIPTION OF THE DRAWINGS

FIG. 13 is a process explanatory view showing the procedure of the method of electrochemically detecting an analyte according to one embodiment of the present invention;

FIG. 14 is a process explanatory view showing the procedure of the method of electrochemically detecting an analyte according to another embodiment of the present invention;

FIG. 15 is a process explanatory view showing the procedure of the modification of the method of electrochemically detecting an analyte shown in FIG. 13;

FIG. 24 is a process explanatory view showing the procedure of the method of electrochemically detecting an analyte in Example 8.

DETAILED DESCRIPTION OF THE PREFERRED EMBODIMENTS

The preferred embodiments of the present invention will be described hereinafter with reference to the drawings.

Term Definition

In explaining the embodiments of the invention, the terms to be used in the present specification will be first defined.

Figure 1:
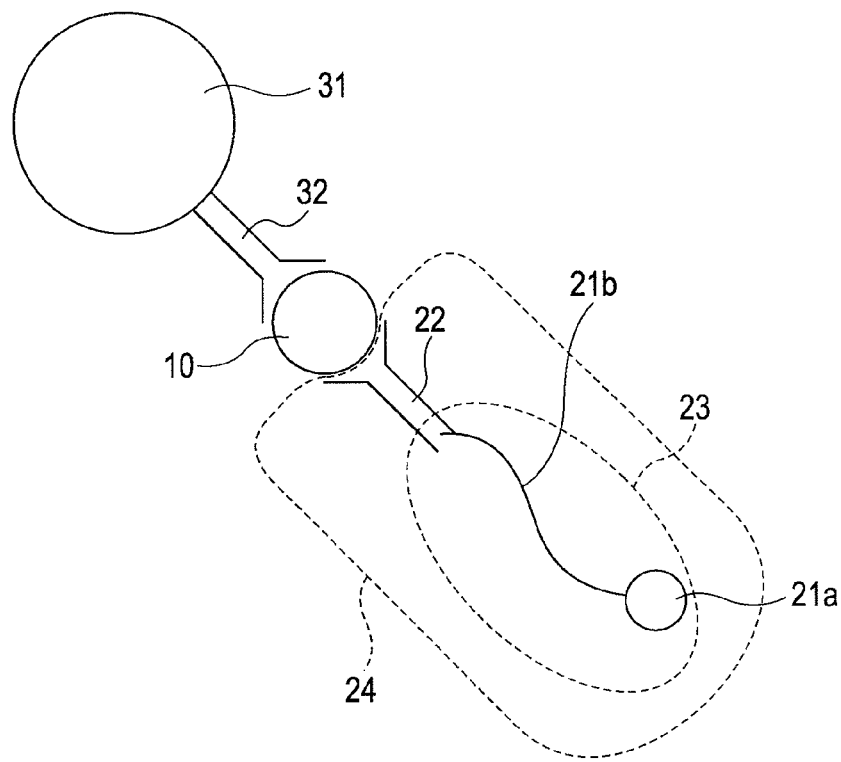
FIG. 1 is an outline explanatory view of a complex containing an analyte and a target substance formed on a solid phase.

The term "target substance which contains a labeling substance" used herein means "a labeling substance 21a only" or "a substance containing the labeling substance 21a and at least one selected from the group consisting of an attractive modulator 21b, a binding substance 22 which traps an analyte 10, the analyte 10, a trapping substance 32 for trapping the analyte 10, and a part of these substances" (see FIG. 1). "substance comprised of the labeling substance 21a and the attractive modulator 21b" is also referred to as a "modified labeling substance" (see 23 in FIG. 1). The term "substance in which the binding substance 22 for trapping the analyte 10 is labeled with the labeling substance 21a" is also referred to as a "label binding substance" (see 24 in FIG. 1). When using a substance which traps the analyte 10 and can be used as the labeling substance, the "label binding substance" may become equivalent to the binding substance 22 which traps the analyte 10 or the labeling substance 21a.

The "solid phase" (31 in FIG. 1) means a support which is used to isolate the analyte. The analyte 10 is trapped on the solid phase 31 through the trapping substance 32 for trapping the analyte 10.

The "attracting liquid" means a solvent which is used for the target substance and a liquid sample for attracting the target substance to near the working electrode.

[Configuration of Detector]

An example of the detector to be used for the method of electrochemically detecting a target substance which contains the labeling substance of the present invention and the method of electrochemically detecting an analyte will be explained with reference to the accompanying drawings.

Figure 2:
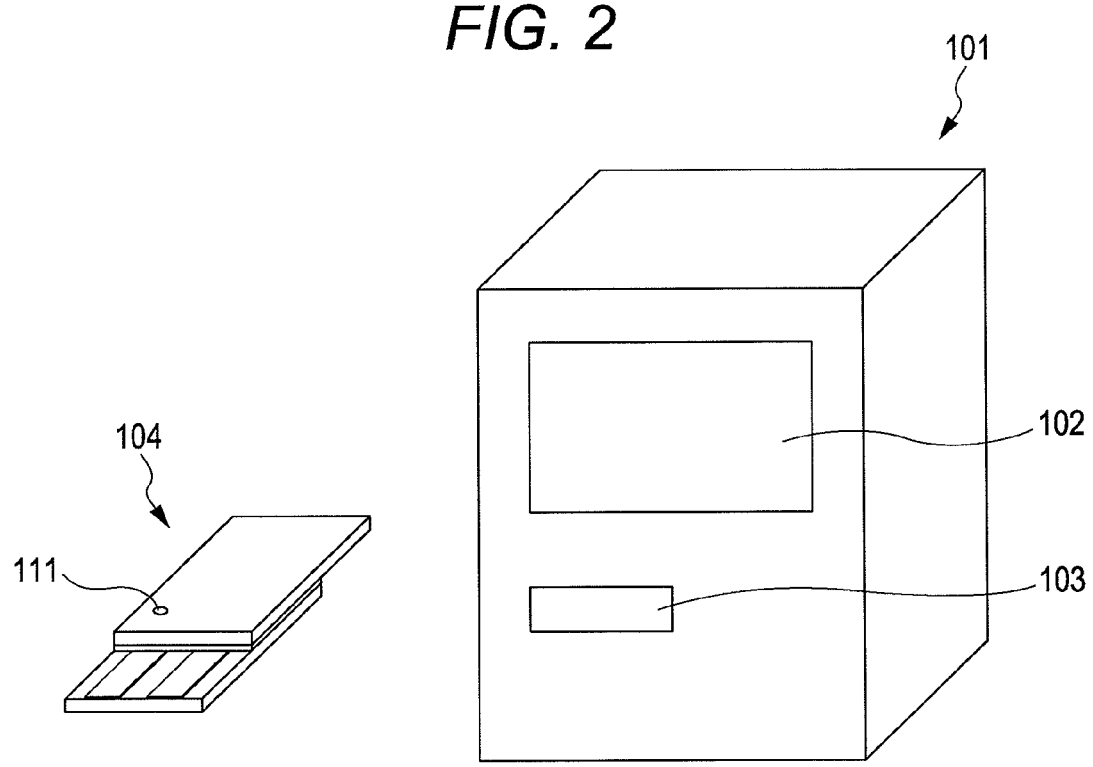
FIG. 2 is a perspective view showing a detector which is used for the method of electrochemically detecting a target substance and the method of electrochemically detecting an analyte according to one embodiment of the present invention.

FIG. 2 is a perspective view showing a detector which is used for the method of electrochemically detecting a target substance which contains a labeling substance and the method of electrochemically detecting an analyte according to one embodiment of the present invention. The detector 101 is used for the electrochemical detection method which photoelectrochemically detects the target substance which contains the labeling substance using a photochemically active substance as a labeling substance.

The detector 101 includes a chip insertion unit 103 into which a test chip 104 is inserted and a display 102 which displays the detection results.

Figure 3:
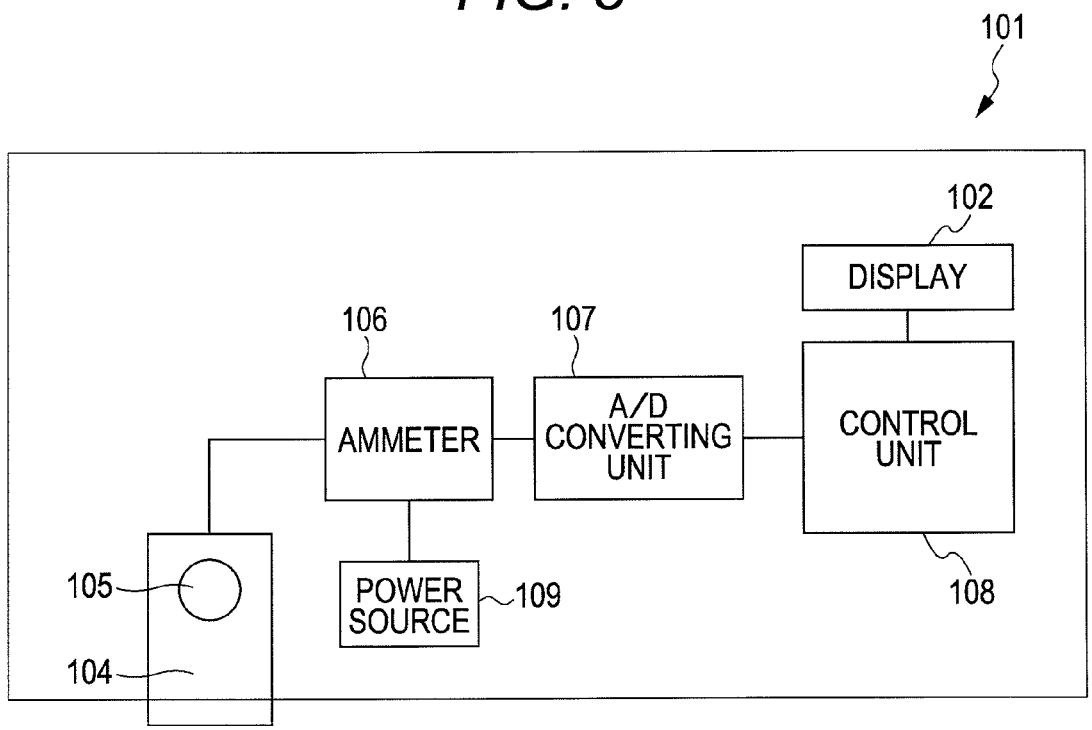
FIG. 3 is a block diagram showing the configuration of the detector shown in FIG. 2.

FIG. 3 is a block diagram showing the configuration of the detector shown in FIG. 2. The detector 101 includes a light source 105, an ammeter (current measuring unit) 106, a power source (potential applying unit) 109, an A/D converting unit 107, a control unit 108, and a display 102.

The light source 105 irradiates the target substance containing the labeling substance which has been transported to near the working electrode of the test chip 104 with light to excite the labeling substance. The ammeter 106 measures an electric current which flows through the test chip 104 due to electrons released from the excited labeling substance. The power source 109 applies a predetermined potential to an electrode formed in the test chip 104. The A/D converting unit 107 digitally converts the current values measured by the ammeter 106. The control unit 108 is configured to include a CPU (Central Processing Unit), a ROM (Read Only Memory), and a RAM (Random Access Memory) and controls the operation of the light source 105, the ammeter 106, the power source 109, and the display 102. The control unit 108 estimates the amount of the target substance containing a labeling substance based on a current value digitally converted by the A/D converting unit 107 and a calibration curve created in advance indicating a relationship between a current value and the amount of the target substance. The display 102 displays the amount of the target substance containing a labeling substance which has been estimated by the control unit 108.

In the present invention, when the target substance containing a labeling substance is detected according to the oxidation reduction current/electrochemiluminescence detection method to be described later, the detector may not include the light source 105 (not shown).

When the target substance containing a labeling substance is detected by electrochemical luminescence, the detector may further include a sensor for detecting light generated from the labeling substance.

[Configuration of Test Chip]

Next, the configuration of the test chip 104 which is used for the method of electrochemically detecting a target substance containing a labeling substance and the method of electrochemically detecting an analyte according to one embodiment of the present invention will be described.

Figure 4:
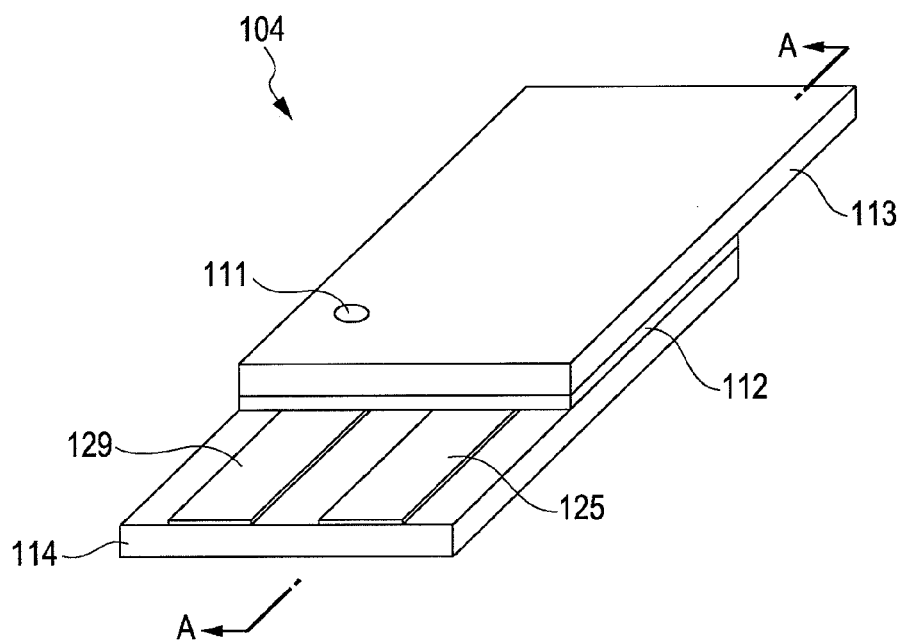
FIG. 4 is a perspective view showing a test chip which is used for the method of electrochemically detecting a target substance and the method of electrochemically detecting an analyte according to one embodiment of the present invention.
Figure 5:
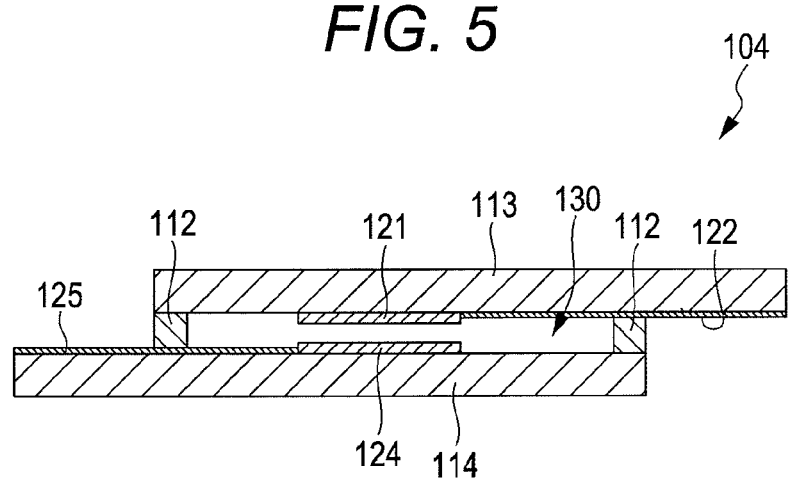
FIG. 5 is a cross-sectional view showing the test chip shown in FIG. 4.

FIG. 4 is a perspective view of the test chip 104 and FIG. 5 is a cross-sectional view (cross-sectional view in an A-A line of FIG. 4) of the test chip 104.

The test chip 104 includes an upper substrate 113, a lower substrate 114 formed at the lower side of the upper substrate 113, and a spacing member 112 which is inserted between the upper substrate 113 and the lower substrate 114.

Figure 6:
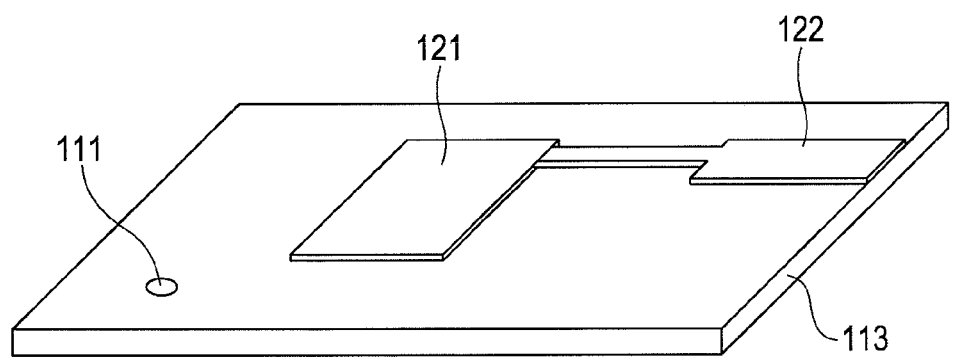
FIG. 6 is a perspective view of the upper substrate of the test chip shown in FIG. 4 as viewed from the lower surface.

FIG. 6 is a perspective view of the upper substrate 113 as viewed from the lower surface. The upper substrate 113 is formed into a rectangular shape. A working electrode 121 and an electrode lead 122 connected to the working electrode 121 are formed on the surface (lower surface) of the upper substrate 113. The working electrode 121 is formed into a nearly rectangular shape and disposed at one side portion of the upper substrate 113 (at the left side of FIG. 6). The electrode lead 122 is extended from the working electrode 121 to the other side portion of the upper substrate 113 (at the right side of FIG. 6).

Figure 7:
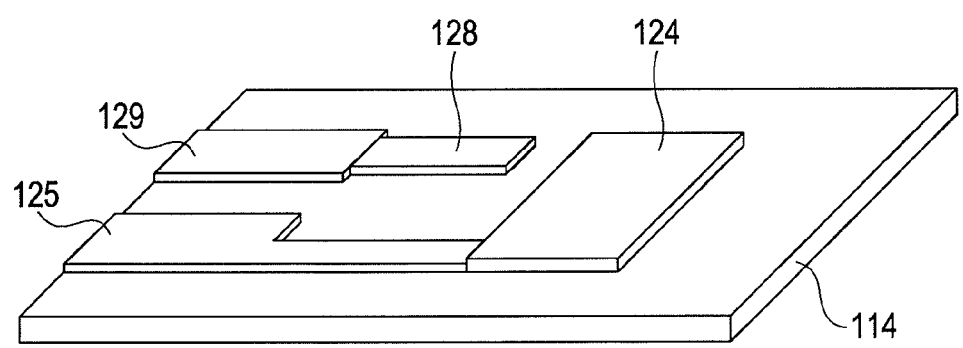
FIG. 7 is a perspective view of the lower substrate of the test chip shown in FIG. 4 as viewed from the upper surface.

FIG. 7 is a perspective view of the lower substrate 114 as viewed from the upper surface. The lower substrate 114 is formed into a rectangular shape with a size nearly similar to that of the upper substrate 113. A counter electrode 124, an electrode lead 125 connected to the counter electrode, a reference electrode 128, and an electrode lead 129 connected to the reference electrode 128 are formed on the surface (upper surface) of the lower substrate 114.

The electrode lead 125 of the counter electrode 124 and the electrode lead 129 of the reference electrode 128 are respectively extended from the one side portion of the lower substrate 114 to the other side portion. The electrode lead 125 of the counter electrode 124 and the electrode lead 129 of the reference electrode 128 are arranged so as to be parallel to each other at the other side portion of the lower substrate 114.

As shown in FIGS. 4 and 5, the upper substrate 113 and the lower substrate 114 are arranged so as to be overlapped at one side portion in such a manner that the formed electrode sections are vertically opposed. The spacing member 112 lies in a portion where the upper substrate 113 and the lower substrate 114 are overlapped (opposed). The electrode leads 122, 125, and 129 formed on the upper substrate 113 and the lower substrate 114 are extruded from the portion where the upper substrate 113 and the lower substrate 114 are overlapped and they are exposed to the outside.

As shown in FIGS. 6 and 7, the spacing member 112 is formed into a rectangular-circular shape and is composed of silicone rubber which is an insulating material. The spacing member 112 is arranged so as to surround a region where the working electrode 121, and the counter electrode 124, and the reference electrode 128 are opposed to one another. A space corresponding to the thickness of a silicone rubber 112 is formed between the upper substrate 113 and the lower substrates 114. Thus, a space 130 for housing a sample and an electrolytic solution (see FIG. 5) is formed among the electrodes 121, 124, and 128. A sample inlet 111 is formed through the upper substrate 113 so that the target substance containing a labeling substance or analyte, and an electrolytic solution, a liquid sample and the like can be injected into the space 130.

In the present embodiment, the working electrode 121 is formed on the surface of the upper substrate 113, and the counter electrode 124 and the reference electrode 128 are formed on the surface of the lower substrate 114. However, the arranging relationship among the working electrode 121, the counter electrode 124, and the reference electrode 128 is not particularly limited as long as each electrode is arranged in the frame of the spacing member 112 without being in contact with other electrodes. For example, the working electrode 121, the counter electrode 124, and the reference electrode 128 may be arranged on the same substrate. The counter electrode 124 may be used as the reference electrode 128 without arranging the reference electrode 128.

Figure 8:
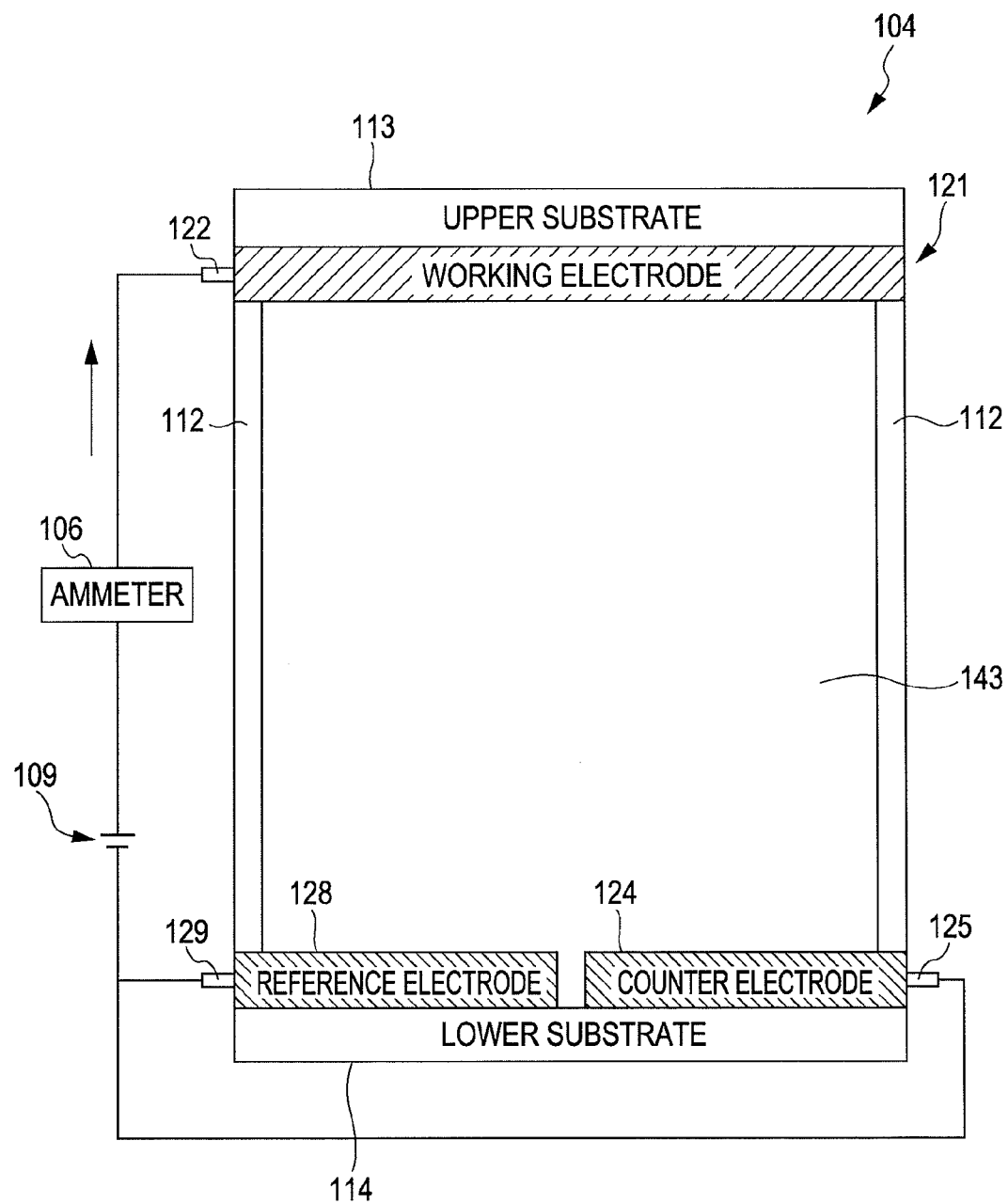
FIG. 8 is an outline view schematically showing an example of an electrode section of the test chip shown in FIG. 4.

FIG. 8 is an outline view schematically showing an example of an electrode section of the test chip 104. The test chip shown in FIG. 8 is used for the oxidation reduction current/electrochemiluminescence detection method to be described later.

In this case, the working electrode 121 may be an electrode which is stable in a solution to be used and has conductivity.

Figure 9:
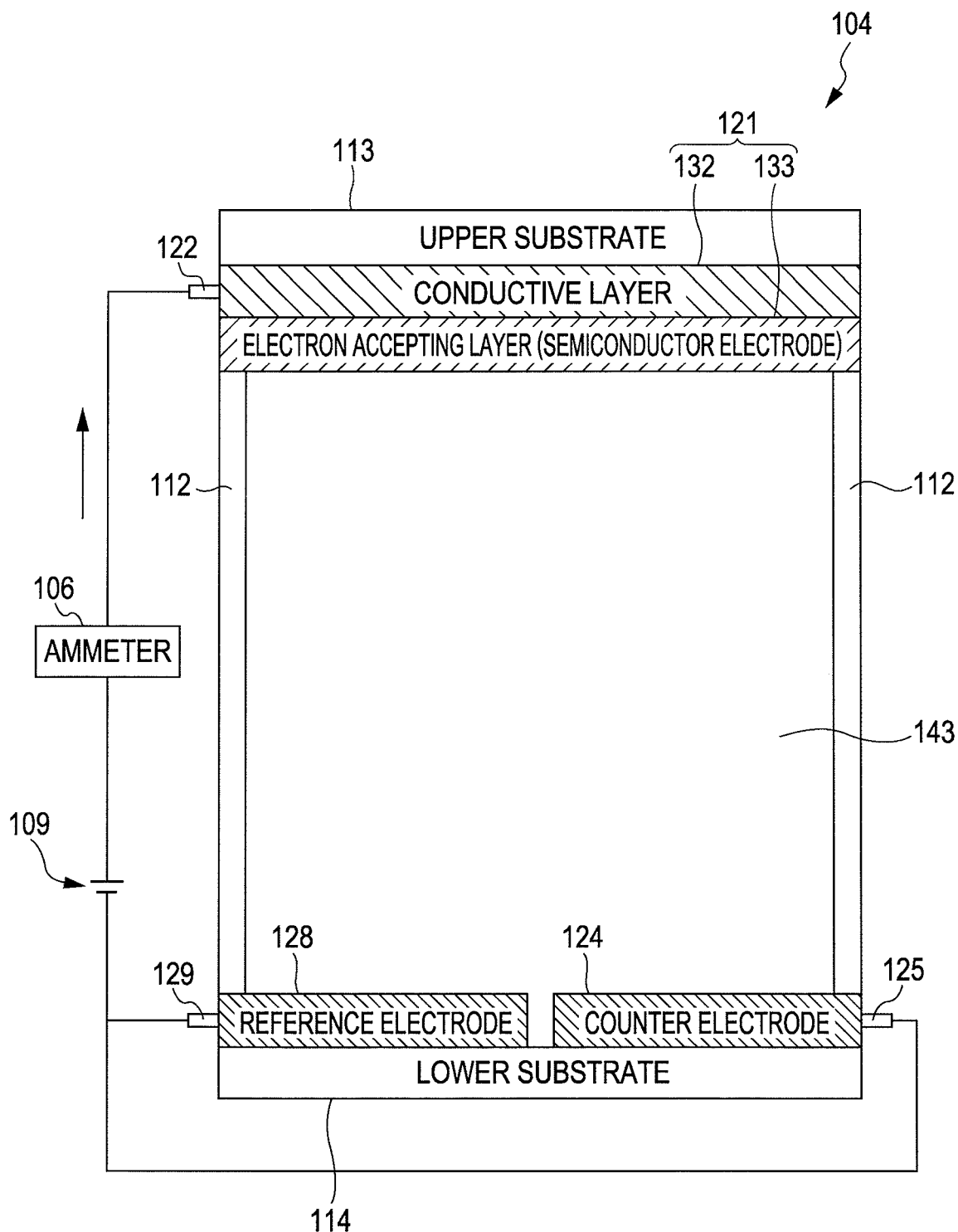
FIG. 9 is an outline view schematically showing another example of the electrode section of the test chip shown in FIG. 4.

On the other hand, when the test chip is used for the photoelectrochemical detection method to be described later, an electrode comprised of a conductive layer 132 formed on the surface of the upper substrate 113 and an electron accepting layer (semiconductor layer; semiconductor electrode) 133 formed on the surface of the conductive layer 132 as shown in FIG. 9 can be used as the working electrode 121.

The conductive layer 132 is composed of a conductive material.

The electron accepting layer 133 contains a substance capable of accepting electrons. The electrode lead 122 of the working electrode 121 is connected to the conductive layer 132.

Unlike the apparatus to be used for the conventional electrochemical detection method, the trapping substance for trapping the target substance containing a labeling substance is not provided on the electron accepting layer 133 of the working electrode 121. Thus, the working electrode 121 does not have the trapping substance which is damaged by washing so that the working electrode 121 can be returned to a reusable state by a simple treatment. Since the test chip 104 which has the working electrode 121 is reusable, it has high economical efficiency as compared to a conventional test chip having a working electrode with the trapping substance immobilized. Therefore, costs for electrochemically detecting the target substance containing a labeling substance or analyte can be reduced. Consequently, the clinical examination and diagnosis can be provided at low cost.

Figure 10:
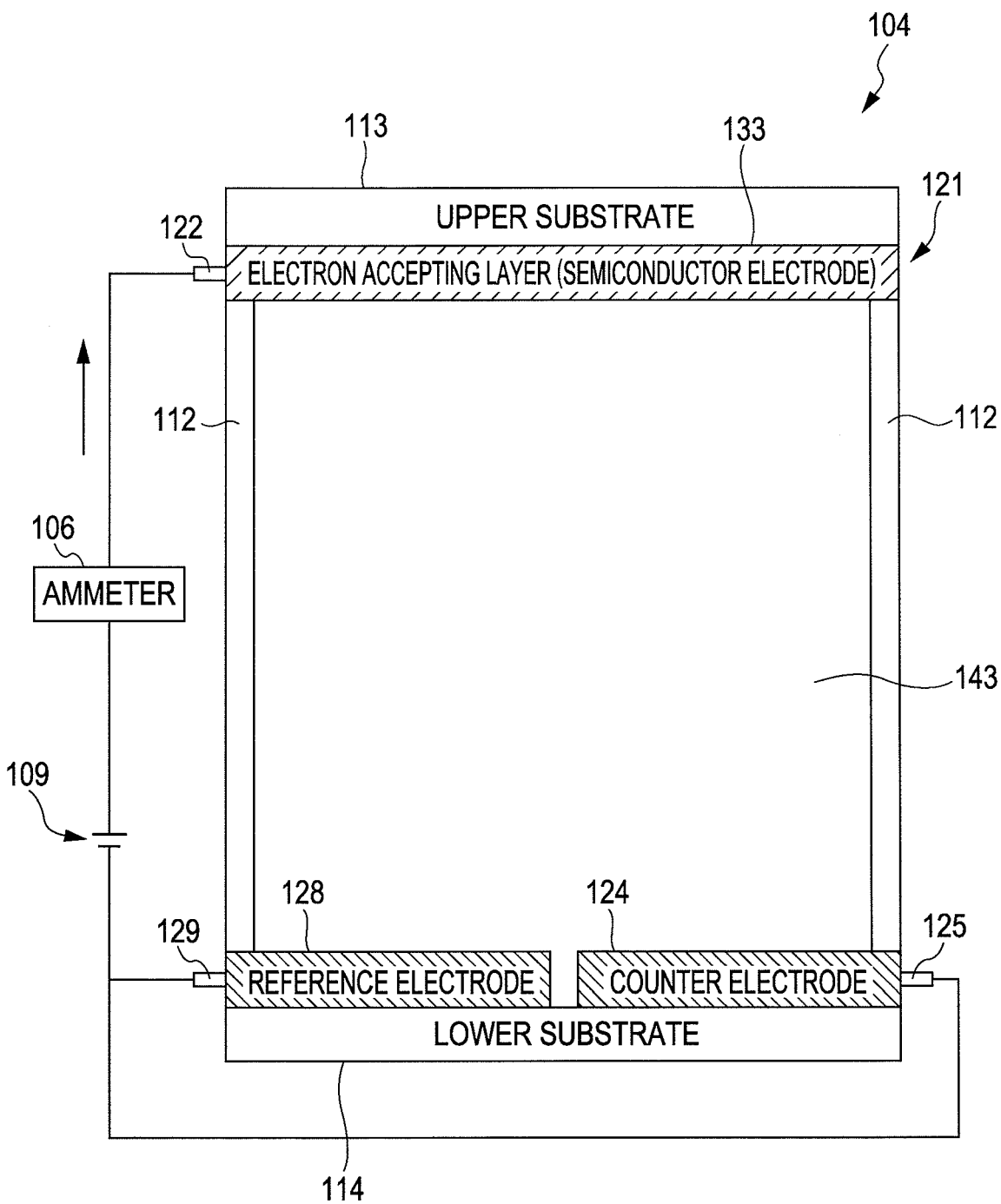
FIG. 10 is an outline view schematically showing another example of the electrode section of the test chip shown in FIG. 4.

In the test chip to be used for the photoelectrochemical detection method to be described later, as shown in FIG. 10, the working electrode 121 may be comprised of the electron accepting layer (semiconductor layer; semiconductor electrode) 133 formed on the surface of the upper substrate 113.

The configuration of these working electrodes can be suitably selected depending on the application of the test chip and the type of the electrochemical detection method. The configuration of the working electrode will be described together with the following electrochemical detection method.

[Method for Electrochemically Detecting Target Substance]

The method of electrochemically detecting a target substance of the present invention is a method of electrochemically detecting the target substance containing a labeling substance which includes attracting the target substance containing a labeling substance in a liquid sample to a working electrode in which a trapping substance for trapping the target substance containing a labeling substance is not present; and electrochemically detecting the target substance containing a labeling substance. In the method of electrochemically detecting a target substance of the present invention, the above described detector and the test chip can be used. However, the present invention is not limited to the above described detector and the test chip. Hereinafter, the "method of electrochemically detecting a target substance" will be sometimes referred to as a "method (A)".

A major characteristic of the method (A) is that the working electrode in which the trapping substance for trapping the target substance containing a labeling substance is not present (see the working electrode 121 in FIGS. 8, 9, and 10) is used. Since the working electrode is reusable, according to the method (A), the detection of the target substance containing a labeling substance can be performed at low cost.

Another characteristic of the method (A) is that the target substance containing a labeling substance is transported to near the working electrode in which the trapping substance for trapping the target substance containing a labeling substance is not present. Accordingly, the target substance containing a labeling substance can be electrochemically detected.

In the method (A), an electrochemically or photochemically active substance is used as the labeling substance. The electrochemically active substance is detected using an oxidation reduction current and/or electrochemical luminescence based on the substance. On the other hand, the photochemically active substance is detected using electrons released by excitation of the substance by light. The method (A) can be divided broadly into the photoelectrochemical detection method (see FIG. 11) and the oxidation reduction current/electrochemiluminescence detection method (FIG. 12) depending on the type of detection technique of the labeling substance.

1. Photoelectrochemical Detection Method

Figure 11C:
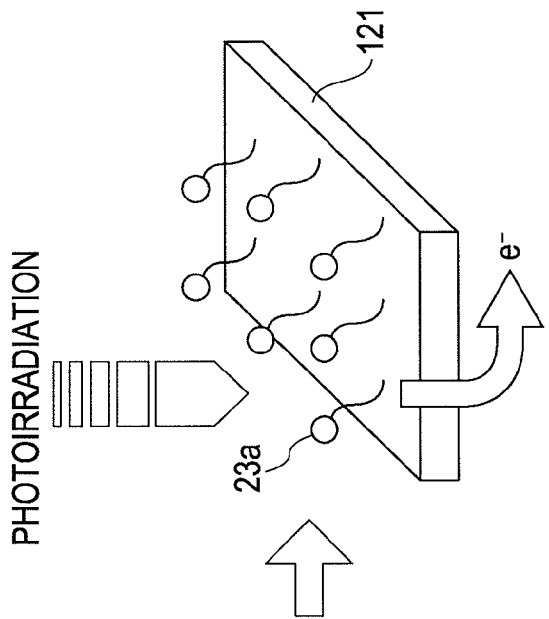
FIG. 11 is a process explanatory view showing the procedure of the method of electrochemically detecting a target substance according to one embodiment of the present invention.
Figure 11B:
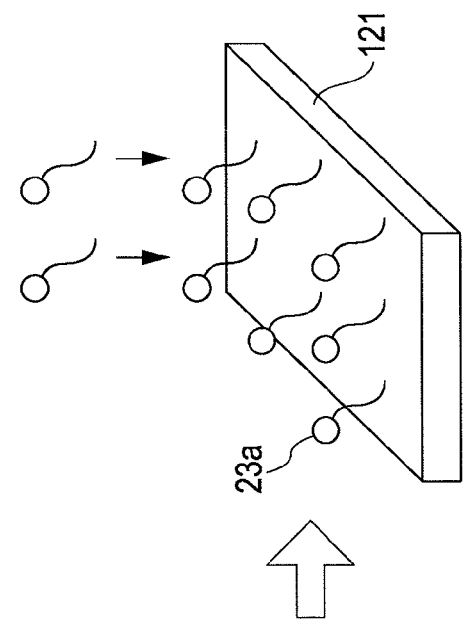
Figure 11A:
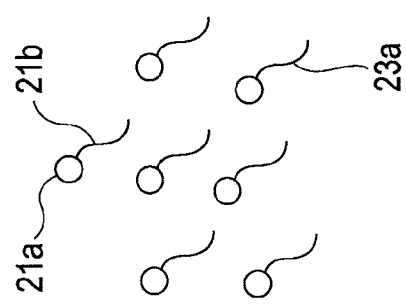

In the photoelectrochemical detection method, the target substance containing a labeling substance is first prepared [see (A) in FIG. 11]. In FIG. 11, the case where a modified labeling substance 23a composed of the labeling substance 21a and the attractive modulator 21b is used as the target substance containing a labeling substance is explained as an example (the same holds true for FIGS. 13 and 15). In the photoelectrochemical detection method, a labeling substance which becomes an excited state by irradiation with light and releases electrons is used as the labeling substance 21a.

As the labeling substance 21a, at least one selected from the group consisting of a metal complex, an organic phosphor, a quantum dot, and an inorganic phosphor can be used.

Specific examples of the labeling substance include metal phthalocyanine dyes, a ruthenium complex, an osmium complex, an iron complex, a zinc complex, 9-phenylxanthene-based dyes, cyanine-based dyes, metallocyanine dyes, xanthene-based dyes, triphenylmethane-based dyes, acridine-based dyes, oxazine-based dyes coumarin-based dyes, merocyanine-based dyes, rhodacyanine-based dyes, polymethine-based dyes, porphyrin-based dyes, phthalocyanine-based dyes, rhodamine-based dyes, xanthene-based dyes, chlorophyl-based dyes, eosine-based dyes, mercurochrome-based dyes, indigo-based dyes, BODIPY-based dyes, CALFluor-based dyes, Oregon green-based dyes, Rhodol green, Texas red, Cascade blue, nucleic acids (DNAs and RNAs), cadmium selenide, cadmium telluride, $Ln_2O_3$:Re, $Ln_2O_2S$:Re, ZnO, $CaWO_4$, $MO.xAl_2O_3$:Eu, $Zn_2SiO_4$:Mn, $LaPO_4$:Ce, Tb, Cy3, Cy3.5, Cy5, Cy5.5, Cy7, Cy7.5, and Cy9 (all products are manufactured by Amersham Biosciences K.K.); Alexa Fluor 355, Alexa Fluor 405, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750 and Alexa Fluor 790 (all products are manufactured by Molecular Probes, Inc.); DY-610, DY-615, DY-630, DY-631, DY-633, DY-635, DY-636, EVOblue10, EVOblue30, DY-647, DY-650, DY-651, DY-800, DYQ-660, and DYQ-661 (all products are manufactured by Dyomics); Atto425, Atto465, Atto488, Atto495, Atto520, Atto532, Atto550, Atto565, Atto590, Atto594, Atto610, Atto611X, Atto620, Atto633, Atto635, Atto637, Atto647, Atto655, Atto680, Atto700, Atto725 and Atto740 (all products are manufactured by Atto-TEC GmbH); and VivoTagS680, VivoTag680, and VivoTagS750 (all products are manufactured by V isEn Medical). Ln represents La, Gd, Lu, or Y, Re represents a lanthanide element, M represents an alkali earth metal element, and x represents a number of 0.5 to 1.5. Concerning other examples of the labeling substance, refer to, for example, U.S. Patent Publication No. 2009/294305, U.S. Pat. No. 5,893,999, and Japanese Patent Application No. 2008-154179.

Examples of the attractive modulator 21b include nucleic acids such as DNAs and RNAs.

If the target substance containing a labeling substance can be attracted to the working electrode, it is not necessary to bind the attractive modulator 21b to the labeling substance 21a.

Since it is easy to attract the target substance containing a labeling substance to the working electrode 121, the substance is preferably a nucleic acid labeled with the labeling substance (labeled nucleic acid).

In the photoelectrochemical detection method, the target substance containing a labeling substance is subsequently attracted to the working electrode 121 ["attracting process" of (B) in FIG. 11].

The attracting process is a process of attracting the target substance containing a labeling substance to a region where electrons can be transported between the target substance and the working electrode in which the trapping substance is not present. In the attracting process, the target substance containing a labeling substance is immobilized on the working electrode.

Here, the term "region where electrons can be transported between the target substance and the working electrode in which the trapping substance is not present" usually means a region ranging from 0 to 10 nm from the working electrode.

The working electrode 121 to be used for the photoelectrochemical detection method is an electrode capable of accepting electrons released by light excitation of the labeling substance 21a. Therefore, the configuration and material of the working electrode 121 are not limited so long as electrons are transported between the working electrode and the labeling substance 21a.

As shown in FIG. 9, the working electrode 121 may be comprised of the conductive layer 132 and the electron accepting layer 133 formed on the surface of the conductive layer 132 or may be comprised of only the electron accepting layer 133 as shown in FIG. 10.

The electron accepting substance for forming the electron accepting layer may be a substance which may have an energy level capable of injecting electrons from the labeling substance 21a excited by light. Here, the term "energy level capable of injecting electrons from the labeling substance 21a excited by light" means a conduction band, for example, when a semiconductor is used as an electron accepting substance. That is, the electron accepting substance may have an energy level lower than an energy level of lowest unoccupied molecular orbital (LUMO) of the labeling substance 21a.

Examples of the electron accepting substance include element semiconductors such as silicon and germanium; oxide semiconductors containing oxides of titanium, tin, zinc, iron, tungsten, zirconium, hafnium, strontium, indium, cerium, yttrium, lanthanum, vanadium, and niobium, tantalum; perovskite-type semiconductors such as strontium titanate, calcium titanate, sodium titanate, vanadium titanate, and potassium niobate; sulfide semiconductors containing sulfides of cadmium, zinc, lead, silver, antimony, and bismuth; semiconductors composed of selenides of cadmium and lead; semiconductors containing telluride of cadmium; semiconductors composed of phosphorus compounds of zinc, gallium, indium, and cadmium; and semiconductors containing compounds such as gallium arsenide, copper-indium selenide, and copper-indium sulfide. The semiconductors may be either intrinsic semiconductors or extrinsic semiconductors.

Among the above semiconductors, the oxide semiconductors are preferred. Among the intrinsic semiconductors of the oxide semiconductors, titanium oxide, zinc oxide, tin oxide, niobium oxide, indium oxide, tungsten oxide, tantalum oxide, and strontium titanate are preferred. Among the extrinsic semiconductors of the oxide semiconductors, indium oxide containing tin and tin oxide containing fluorine are preferred. Indium oxide containing tin or tin oxide containing fluorine has characteristics of functioning not only as an electron accepting substance, but also as a conductive base material. Thus, the use of these materials allows only the electron accepting layer to function as the working electrode without using the conductive base material.

The conductive base material for forming the conductive layer 132 may be a composite base material in which a conductive material layer composed of a material having conductivity is formed on the surface of a nonconductive base material composed of nonconductive substances such as glass and plastics. The shape of the conductive material layer may be filmy or spot-like.

When the composite base material is used, the electron accepting layer 133 is formed on the conductive material layer. Examples of the material having conductivity for forming the conductive material layer include metals such as platinum, gold, silver, copper, aluminium, rhodium, and indium; electrically conductive ceramics of carbon, carbide, and nitride; conductive metal oxides such as indium oxide containing tin, tin oxide containing fluorine, tin oxide containing antimony, zinc oxide containing gallium, and zinc oxide containing aluminium. Among them, indium oxide containing tin and tin oxide containing fluorine are preferred.

The conductive base material is not particularly limited as long as it can ensure conductivity. Therefore, a conductive material layer which does not have strength as a support in itself is also included in the conductive base material.

As described above, when the electron accepting substance to be used for the electron accepting layer 133 is a substance which functions as the conductive base material, the working electrode 121 may not have the conductive layer 132.

The working electrode 121 may be subjected to surface treatment using a silane coupling agent. The surface of the working electrode 121 can be suitably adjusted so as to be hydrophilic or hydrophobic by the surface treatment. Examples of the silane coupling agent include cationic silane coupling agents such as aminopropyl triethoxysilane (APTES).

The attraction of the target substance containing a labeling substance to the working electrode 121 is achieved by hydrophobic or hydrophilic interaction among the target substance, the attracting liquid, and the working electrode or electrophoretic effects caused by applying a voltage to the working electrode or the counter electrode.

The attracting process is performed by, for example, 1) changing the hydrophobicity and hydrophilicity of the attracting liquid to increase hydrophobic or hydrophilic interaction between the target substance and the working electrodes 121 [i.e., attracting the target substance containing a labeling substance to the working electrode in which the trapping substance is not present (the working electrode 121) by differences in polarity] (the attraction method 1); and 2) applying a positive or negative voltage to the working electrode 121 to increase electrophoretic effects depending on the charge of the target substance containing a labeling substance [i.e., attracting the target substance containing a labeling substance to the working electrode (working electrode 121) in which the trapping substance is not present by using the electrophoretic effects] (the attraction method 2). The attraction methods 1 and 2 may be performed independently or in combination with each other.

In the attraction method 1, when nucleic acid is used as the attractive modulator 21b, it is preferable that the attracting liquid contains a chaotropic ion from the viewpoint of increasing hydrophobic or hydrophilic interaction between the target substance and the working electrode 121 and easily attracting the target substance to near the working electrode 121.

Examples of the chaotropic ion include an iodide ion, a bromide ion, a guanidine ion, a thiocyanic acid ion, a tribromoacetic acid ion, a trichloroacetic acid ion, a perchlorate ion, a dichloroacetic acid ion, a nitrate ion, a chloride ion, an acetate ion, a barium ion, a calcium ion, a lithium ion, a cesium ion, a potassium ion, and a magnesium ion.

When the attracting liquid contains the chaotropic ion, the concentration of chaotropic ion in the attracting liquid varies depending on the type of chaotropic ion to be used. The concentration is usually from 1.0 to 8.0 mol/L. When the chaotropic ion is a guanidine ion, the concentration of chaotropic ion in the attracting liquid is usually from 4.0 to 7.5 mol/L. When the chaotropic ion is a thiocyanic acid ion, the concentration of chaotropic ion in the attracting liquid is usually from 3.0 to 5.5 mol/L.

When nucleic acids (DNAs and RNAs) are used as the labeling substance 21a or the attractive modulator 21b, the target substance containing a labeling substance can be attracted to near the working electrode 121 by using conventional methods for extracting and purifying nucleic acids.

Examples of the method of extracting and purifying nucleic acids include a method of using a liquid phase and a method of using a carrier for binding nucleic acids. Examples of the method of using a liquid phase include a phenol/chloroform extraction method (Biochimica et Biophysica acta, vol. 72, pp. 619-629 (1963)), an alkali-SDS method (Nucleic Acid Research, vol. 7, pp. 1513-1523 (1979)), and a method of adding ethanol to a buffer containing guanidine hydrochloride to precipitate nucleic acids (Analytical Biochemistry, 162, 1987, 463). Examples of the method of using a carrier for binding nucleic acids include a method of isolating nucleic acids comprising: adsorbing nucleic acids to glass particles by using the glass particles and a sodium iodide solution (Proc. Natl. Acad. Sci. USA, 76-2:615-619-1979) and a method of using silica particles and chaotropic ions [see, for example, J. Clinical. Microbiology, vol. 28, pp. 495-503 (1990) and U.S. Pat. No. 5,234,809]. In the method of using silica particles and chaotropic ions, a solution which contains chaotropic ions capable of releasing nucleic acids in a sample and silica particles to which nucleic acids are bound is first mixed with the sample in order to bind nucleic acids to silica particles. Next, impurities are removed by washing. Thereafter, the nucleic acids bound to silica particles are recovered. According to the method, the nucleic acids can be extracted simply and rapidly. Additionally, the method is suitable for not only the extraction of DNA, but also for extraction of RNA which is more unstable, and is very excellent in terms of obtaining nucleic acids with high purity.

When the target substance containing a labeling substance contains nucleic acid as the labeling substance 21a or the attractive modulator 21b, the target substance can be attracted to near the working electrode 121 by using a solvent to be used for the method of extracting and purifying nucleic acids as an attracting liquid. In this case, it is preferable that a guanidine ion, an iodide ion, bromide ion, and a thiocyanic acid ion or an arbitrary combination thereof is used as the chaotropic ion and an electrode for binding nucleic acids (for example, indium oxide containing tin) is used as the working electrode.

When the target substance containing a labeling substance contains nucleic acids (DNAs and RNAs) as the labeling substance 21a or the attractive modulator 21b, the attracting liquid may contain a buffer, if necessary. The buffer may be a buffer which is generally used to hold nucleic acids stably. It is preferable that the buffer has a buffer capacity at a neutral pH, i.e., at a pH of 5.0 to 9.0 from the viewpoint of holding nucleic acids stably. Examples of the buffer include Tris-HCL salt, sodium-tetraborate-hydrochloric acid, and potassium dihydrogenphosphate-sodiumtetraborate. The concentration of the buffer is preferably from 1 to 500 mmol/L.

On the other hand, in the attraction method 2, positive or negative voltage is applied to the working electrode depending on the charge of the target substance containing a labeling substance. For example, when the target substance containing a labeling substance contains nucleic acid as the labeling substance 21a or the attractive modulator 21b, the nucleic acid is negatively charged. Therefore, the target substance containing a labeling substance can be attracted to near the working electrode 121 by applying a positive voltage to the working electrode 121.

In the photoelectrochemical detection method, subsequently, the target substance is detected by irradiating the target substance containing a labeling substance, which is present near the working electrode 121, with light to excite the labeling substance 21a and measuring the photocurrent [(C) in FIG. 11, "detection process]".

In the detection process, when the attracting liquid is used in the attracting process, the attracting liquid can be substituted for an electrolytic solution suitable for the electrochemical detection, if necessary. In this case, the target substance containing a labeling substance is electrochemically detected in the presence of the electrolytic solution. When the attracting liquid has characteristics of supplying electrons to the labeling substance 21a in an oxidized state and the electrochemical detection of the target substance is possible, the attracting liquid may be used with no change in the detection process.

As the electrolytic solution, a solution containing an electrolyte composed of salts which may supply electrons to the labeling substance 21a in an oxidized state, an aprotic polar solvent, a protonic polar solvent, or a mixture of the aprotic polar solvent and the protonic polar solvent can be used. The electrolytic solution may further contain other components, if desired.

Examples of the electrolyte include iodide, bromide, a metal complex, thiosulfate, sulfite, and a mixture thereof. Specific examples of the electrolyte include metal iodides such as LiI, NaI, KI, CsI, and $CaI_2$; iodine salts of quaternary ammonium compounds such as tetraalkylammonium iodide, pyridinium iodide, imidazolium iodide; metal bromides such as LiBr, NaBr, KBr, CsBr, and $CaBr_2$; bromine salts of quaternary ammonium compounds such as tetraalkylammonium bromide and pyridinium bromide; metal complexes such as a ferrocyanic acid salt and a ferricinium ion; thiosulfates such as sodium thiosulfate, ammonium thiosulfate, potassium thiosulfate, and calcium thiosulfurate; sulfites such as sodium sulfite, potassium sulfite, ammonium sulfite, iron sulfite, sodium hydrogensulfite, and calcium sulfite; and a mixture thereof. Among them, tetrapropylammonium iodide and $CaI_2$ are preferred.

The electrolyte concentration of the electrolytic solution is preferably from 0.001 to 15 M.

Water, a polar solvent containing a buffer component and amain component of water, or the like may be used as the protonic polar solvent.

Examples of the aprotic polar solvent include nitriles such as acetonitrile ($CH_3CN$); carbonates such as propylene carbonate and ethylene carbonate; heterocyclic compounds such as 1,3-dimethylimidazolinone, 3-methyloxazolinone and dialkylimidazolium salt; dimethylformamide, dimethyl sulfoxide, and sulfolane. Among the aprotic polar solvents, acetonitrile is preferred. The protonic polar solvent and the aprotic polar solvent can be used alone or mixed for use. As a mixture of the protonic polar solvent and the aprotic polar solvent, a mixture of water and acetonitrile is preferred.

When the target substance containing a labeling substance is irradiated with light, a light source which can emit light in a wavelength capable of photoexciting the labeling substance can be used. The light source can be suitably selected depending on the type of the labeling substance. Examples of the light source include fluorescent lamps, black light, bactericidal lamps, incandescent lamps, low-pressure mercury lamps, high-pressure mercury lamps, xenon lamps, mercury-xenon lamps, halogen lamps, metal halide lamps, light emitting diodes (white LED, blue LED, green LED, and red LED), lasers (carbon dioxide lasers, dye lasers, semiconductor lasers), and sunlight. Among the light sources, fluorescent lamps, incandescent lamps, xenon lamps, halogen lamps, metal halide lamps, light emitting diodes, and sunlight are preferred. In the detection process, the target substance containing a labeling substance may be irradiated with only light in a specified wavelength region using a spectrometer or a bandpass filter, if necessary.

In the measurement of a photocurrent derived from the target substance containing a labeling substance, for example, a measurement device which includes an ammeter, a potentiostat, a recorder, and a computer can be used.

In the detection process, the amount of the target substance can be examined by quantifying the photocurrent.

The trapping substance for trapping the target substance containing a labeling substance is not present on the working electrode 121 to be used for the photoelectrochemical detection. Therefore, the working electrode 121 can be cleaned by a simple treatment so that it is reusable.

The cleaning of the working electrode can be performed by ultraviolet ray-ozone cleaning (UV-$O_3$ cleaning) or the like. In the UV-$O_3$ cleaning, an organic compound is decomposed by a powerful oxidation effect in processes of decomposition of the organic compound by ultraviolet rays and formation and decomposition of $O_3$, and it is removed from the surface of the electrode.

When nucleic acid is used as the labeling substance 21a or the attractive modulator 21b, the target substance can also be dissociated from the working electrode by applying a negative voltage to the working electrode in a suitable solution. This is because the nucleic acid is negatively charged. Examples of the solution include phosphate-buffered saline (PBS), TEB [composition: 10 mM Tris-HCL buffer, 1 mM EDTA], and water.

2. Oxidation Reduction Current/Electrochemiluminescence Detection Method

Figure 12A:
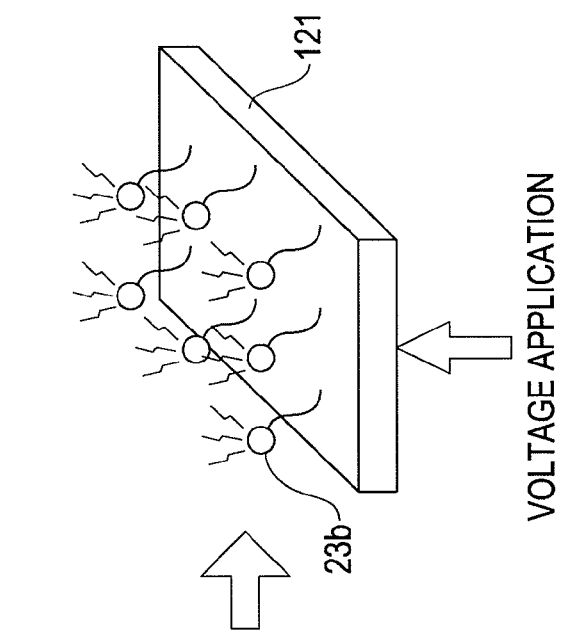
FIG. 12 is a process explanatory view showing the procedure of the method of electrochemically detecting a target substance according to another embodiment of the present invention.
Figure 12B:
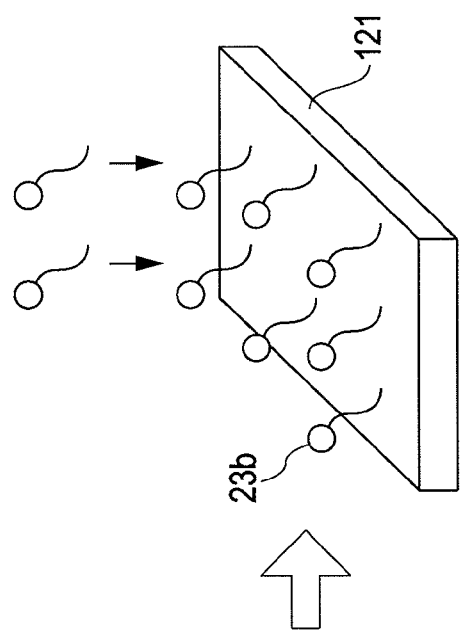
Figure 12C:
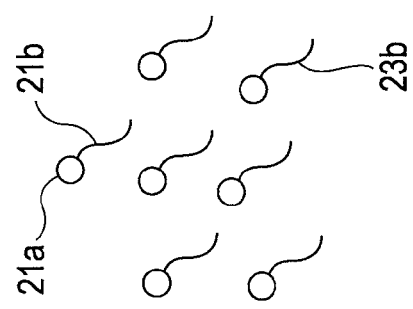
Figure 16A:
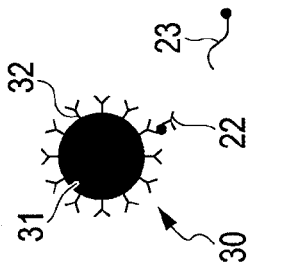
FIG. 16 is a process explanatory view showing the procedure of the modification of the method of electrochemically detecting an analyte shown in FIG. 14.
Figure 16B:
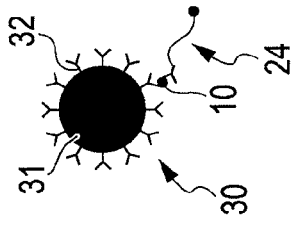
Figure 16C:
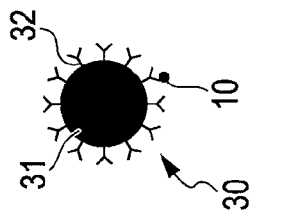
Figure 16D:
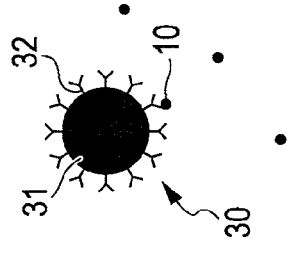
Figure 16E:
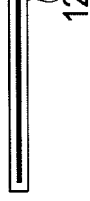
Figure 16F:
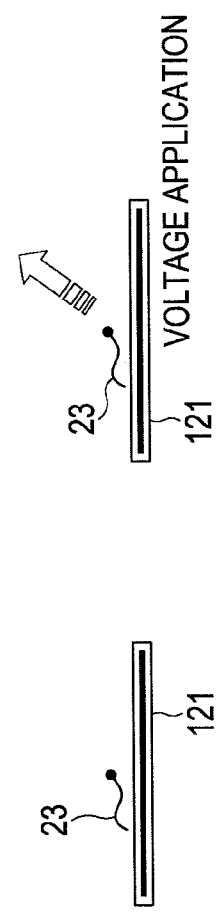

In the oxidation reduction current/electrochemiluminescence detection method, the target substance containing a labeling substance is first prepared in the same manner as the case of the photoelectrochemical detection method. In FIG. 12, the method will be described taking an example of the case where the modified labeling substance 23a composed of the labeling substance 21a and the attractive modulator 21b is used as the target substance containing a labeling substance (the same holds true for FIGS. 14 and 16). In the oxidation reduction current/electrochemiluminescence detection method, a labeling substance which generates oxidation reduction current when a voltage is applied or a labeling substance which emits light when a voltage is applied is used as the labeling substance 21a.

Examples of the labeling substance which generates oxidation reduction current when a voltage is applied include metal complexes containing metal which causes an electrically reversible oxidation-reduction reaction as a central metal. Examples of the metal complexes include tris(phenanthroline) zinc complex, tris(phenanthroline) ruthenium complex, tris(phenanthroline) cobalt complex, di(phenanthroline) zinc complex, di(phenanthroline) ruthenium complex, di(phenanthroline) cobalt complex, bipyridine platinum complex, terpyridine platinum complex, phenanthroline platinum complex, tris(bipyridyl) zinc complex, tris(bipyridyl) ruthenium complex, tris(bipyridyl) cobalt complex, di(bipyridyl) zinc complex, di(bipyridyl) ruthenium complex, and di(bipyridyl) cobalt complex.

In the oxidation reduction current/electrochemiluminescence detection method, nucleic acid which can be used as the attractive modulator may be used as the labeling substance. When nucleic acid is used as the labeling substance, oxidation reduction current derived from adenine, thymine, guanine, cytosine, or uracil can be used as the oxidation reduction current derived from the nucleic acid.

Examples of the labeling substance which emits light when a voltage is applied include luminol, lucigenin, pyrene, diphenylanthracene, and rubrene. Luminescence of these labeling substances can be enhanced by using enhancer, for example, luciferin derivatives such as firefly luciferin and dehydroluciferin, phenols such as phenylphenol and chlorophenol or naphthos.

In the oxidation reduction current/electrochemiluminescence detection method, the target substance containing a labeling substance is subsequently attracted to the working electrode 121 ["attracting process", (B) in FIG. 12].

The attracting process is a process of attracting the labeling substance to a region where the electronic excitation occurs by the working electrode in which the trapping substance is not present.

The attraction of the target substance containing a labeling substance to the working electrode 121 can be performed by the same operation as that of the attracting process in the photoelectrochemical detection method.

Here, the term "region where the electronic excitation occurs by the working electrode in which the trapping substance is not present" is a region where electrons are transferred from the working electrode to the labeling substance by applying a voltage and the labeling substance can get into an electronically excited state. The region is usually a region ranging from 0 to 10 nm from the working electrode.

Examples of the working electrode 121 (see FIG. 9) to be used for the oxidation reduction current/electrochemiluminescence detection method include carbon electrodes composed of graphite, glassy carbon, pyrolytic graphite, carbon paste, carbon fiber, or the like; noble metal electrodes composed of platinum, platinum black, gold, palladium, rhodium, or the like; oxide electrodes composed of titanium oxide, tin oxide, manganese oxide, lead oxide, or the like; semiconductor electrodes composed of Si, Ge, ZnO, CdS, $TiO_2$, GaAs, or the like as electronically important materials; and titanium electrodes composed of titanium.

The working electrode 121 to be used for the oxidation reduction current/electrochemiluminescence detection method may be subjected to surface treatment using a cationic silane coupling agent such as aminopropyl triethoxysilane (APTES) as a silane coupling agent in the same manner as the case of the working electrode 121 to be used for the photoelectrochemical detection method. The surface of the working electrode 121 can be suitably adjusted so as to be hydrophilic or hydrophobic by the surface treatment.

In the oxidation reduction current/electrochemiluminescence detection method, a voltage is subsequently applied to the target substance containing a labeling substance which is present near the working electrode 121. Then, the target substance is detected by measuring the oxidation reduction current or light based on the labeling substance ["detection process", (C) in FIG. 12]. (C) in FIG. 12 is shown taking an example of the case of measuring light.

In the detection process, when the attracting liquid is used in the attracting process, the attracting liquid can be substituted for an electrolytic solution suitable for the electrochemical detection in the same manner as the case of the photoelectrochemical detection method, if necessary. In this case, the target substance containing a labeling substance is electrochemically detected in the presence of the electrolytic solution.

When measuring the oxidation reduction current in the detection process, a measurement device which includes for example, a potentiostat, a function generator, a recorder, and a computer can be used.

In this case, the amount of the target substance can be examined by quantifying the oxidation reduction current.

When measuring the light based on the labeling substance in the detection process, a photon counter can be used for the measurement of the light. In this case, the light can be indirectly detected by using an optical fiber electrode obtained by forming a transparent electrode at the end of an optical fiber in place of the electrode (see U.S. Pat. No. 5,776,672 and U.S. Pat. No. 5,972,692).

The trapping substance for trapping the target substance containing a labeling substance is also not present on the working electrode 121 to be used for the oxidation reduction current/electrochemiluminescence detection method. Therefore, the working electrode 121 can be cleaned by a simple treatment in the same manner as the case where the working electrode 121 to be used for the photoelectrochemical detection method so that it is reusable.

The process of cleaning the working electrode can be performed by the same operation as the process of cleaning the working electrode in the photoelectrochemical detection method.

[Method for Electrochemically Detecting Analyte]

The method of electrochemically detecting an analyte of the present invention is a method of electrochemically detecting an analyte, comprising: forming a complex containing a labeling substance and an analyte on a solid phase; isolating the solid phase in which the complex is formed; separating a target substance containing a labeling substance from the complex formed on solid phase which is obtained in the isolation process; attracting the separated target substance containing a labeling substance to a working electrode in which a trapping substance for trapping the target substance containing a labeling substance is not present; and electrochemically detecting the target substance containing a labeling substance.

The above-described detector and test chip can be used for the method of electrochemically detecting an analyte of the present invention. However, the present invention is not limited to the above-described detector and test chip. Hereinafter, the "method of electrochemically detecting an analyte" may be indicated as the "method (B)".

In the method (B), an electrochemical or photochemically active substance is used as the labeling substance. The method (B) can be divided broadly into the photoelectrochemical detection method (see FIG. 13) and the oxidation reduction current/electrochemiluminescence detection method (FIG. 14) depending on the type of detection technique of the labeling substance in the same manner as the case of the method (A).

The method (B) is different from the method (A) in that a process of obtaining a target substance containing a labeling substance depending on the amount of analyte ["a process of trapping an analyte" ((A) in FIGS. 13 and 14), "a process of adding a target substance" ((B) in FIGS. 13 and 14), "an isolation process" ((C) in FIG. 13 and FIG. 14), and "a separation process" ((D) in FIGS. 13 and 14)] are included.

In the method (B), the attraction process [see (E) in FIGS. 13 and 14] and the detection process [see (F) in FIGS. 13 and 14] are the same as those of the attraction process and the detection process in the method (A). The labeling substance, the attractive modulator, the attracting liquid, the working electrode, and the electrolytic solution which are used for the method (B) are the same as those used for the method (A).

Hereinafter, the process of obtaining a target substance containing a labeling substance depending on the amount of analyte in the method (B) will be described.

In the method (B), the analyte 10 is first trapped on the solid phase 31 through the trapping substance (the first trapping substance 32 [(A) in FIGS. 13 and 14, the "process of trapping an analyte"]. In the process of trapping an analyte, a complex containing the first trapping substance 32 and the analyte 10 is formed on the solid phase 31. In this case, components other than the analyte 10 are not trapped by the first trapping substance 32 and they are in the free state.

The solid phase 31 may be a solid phase which can be isolated by a magnetic separation process or a solution substitution process. Examples of the solid phase 31 include magnetic beads and substrates.

The first trapping substance 32 can be suitably selected depending on the type of the analyte 10. For example, when the analyte 10 is a nucleic acid, the first trapping substance 32 is a nucleic acid probe which is hybridized to the nucleic acid or an antibody against the nucleic acid. When the analyte 10 is a protein or a peptide, the first trapping substance 32 may be an antibody against the protein or peptide, a ligand against the protein, a receptor protein against the peptide or the like.

The process of trapping the analyte 10 by the first trapping substance 32 can be performed under conditions where the first trapping substance 32 is bound to the analyte 10. The conditions where the first trapping substance 32 is bound to the analyte 10 can be suitably selected depending on the type of the analyte 10 and the type of the solid phase 31.

For example, when the analyte is a nucleic acid, the process of trapping the analyte 10 by the first trapping substance 32 can be performed in a solution such as phosphate-buffered saline. The process of trapping the analyte 10 by the first trapping substance 32 can be performed in, for example, a microtube (e.g. an Eppendorf tube).

Then, the target substance (a label binding substance 24) containing a labeling substance is added to the analyte 10 [(B) of FIGS. 13 and 14, a "process of adding a target substance]".

The process of adding the target substance (the label binding substance 24) containing a labeling substance to the analyte 10 can be performed under conditions where the binding substance 22 contained in the label binding substance 24 is bound to the analyte 10. The conditions where the binding substance 22 is bound to the analyte 10 can be suitably selected depending on the type of the analyte 10.

For example, when the analyte is a nucleic acid, the process of adding the target substance (the label binding substance 24) containing a labeling substance to the analyte 10 can be performed in a solution such as phosphate-buffered saline. The process of adding the target substance (the label binding substance 24) containing a labeling substance to the analyte 10 can be performed in, for example, a microtube (e.g. an Eppendorf tube).

When the analyte 10 is a nucleic acid, the nucleic acid which contains a recognition sequence capable of being cleaved by a restriction enzyme in a portion that is not involved in the trapping of the analyte and has the labeling substance bounded (also referred to as a "cleavable nucleic acid") can be used. In this case, a complex which contains at least the first trapping substance 32, the analyte 10, and the labeling substance is formed on the solid phase 31. Therefore, the target substance containing a labeling substance depending on the amount of the analyte can be easily obtained by using the restriction enzyme in the separation process to be described later.

When the analyte 10 is a nucleic acid and the nucleic acid is contained in the target substance containing a labeling substance, a complex formed on the solid phase 31 may be heated in the separation process to be described later. Thus, the target substance containing a labeling substance can be easily obtained depending on the amount of the analyte.

In the process of adding the target substance, a substance which recognizes and traps a complex containing the first trapping substance 32 and the analyte 10 formed on the solid phase 31 may be used as the target substance containing a labeling substance.

For example, when the analyte 10 is a nucleic acid and the first trapping substance 32 contains the nucleic acid, examples of the target substance containing a labeling substance include intercalating agents which recognize double strand nucleic acids. The intercalating agent has a plate-like insertion group, such as a phenyl group, in its molecule. The plate-like insertion group is inserted between a base pair of double strand nucleic acid (a complex of the analyte 10 and the first trapping substance 32) and a base pair. Thus, the intercalating agent is bound to the double strand nucleic acid.

Examples of the intercalating agent include an intercalating agent (an electrochemically active substance) which changes electrochemically and an intercalating agent which changes optically (a photochemically active substance). The double strand nucleic acid to which these intercalating agents are bonded can be detected by measuring electrochemical or optical changes in the intercalating agents. Therefore, the intercalating agent that changes electrochemically or the intercalating agent that changes optically may be used as the labeling substance. The intercalating agent is not particularly limited and usable examples thereof include ethidium, ethidium bromide, acridine, aminoacridine, acridine orange, proflavine, ellipticine, actinomycin-D, daunomycin, and mitomycin-C. Other usable intercalating agents include intercalating agents described in U.S. Pat. No. 4,968,602, U.S. Pat. No. 5,776,672, and U.S. Pat. No. 5,972,692.

Subsequently, the solid phase 31 with the complex formed is isolated [(C) of FIGS. 13 and 14, the "isolation process]".

In the isolation process, the method of isolating the solid phase 31 can be suitably selected depending on the type of the solid phase 31.

For example, when the solid phase 31 is a magnetic bead, the solid phase 31 (magnetic bead) is attracted to a magnet. In this case, the solid phase 31 (magnetic bead) can be easily isolated by using the magnet.

When the solid phase 31 is a substrate, components other than the analyte 10 can be removed by replacing a solution on the substrate with a new solution. In this case, the solid phase 31 can be easily isolated by substitution of the solution on the substrate.

Subsequently, the target substance containing a labeling substance (a modified labeling substance 23 in (D) in FIGS. 13 and 14) is separated from the complex formed on the solid phase 31 which has been obtained in the isolation process [(D) of FIGS. 13 and 14, the "separation process"].

In the separation process, the target substance containing a labeling substance is separated by the separation method according to the type of the target substance containing a labeling substance (the label binding substance 24) which has been used in the process of adding the target substance.

For example, when the analyte 10 is a nucleic acid and a labeling substance in which a nucleic acid having a sequence complementary to the analyte is modified is used, the target substance containing a labeling substance depending on the amount of the analyte can be easily separated from the solid phase by heating a solution containing the complex formed on the solid phase 31.

When the labeling substance is modified with the cleavable nucleic acid, the target substance containing a labeling substance depending on the amount of the analyte can be obtained by cleaving the recognition sequence in the cleavable nucleic acid with the restriction enzyme.

As described above, when the nucleic acid is contained in the target substance containing a labeling substance, a solution to be used for the extraction and purification of nucleic acid (e.g. trade name: PB buffer, manufactured by QIAGEN) can be used in the attracting process. In this case, the solution is first added to the liquid phase recovered in the separation process. Then, the obtained mixture is added dropwise to the working electrode 121. As a result, the target substance (the modified labeling substance 23) containing a labeling substance can be attracted to near the working electrode 121.

When the analyte is substances other than nucleic acids, a nucleic acid may be used as the labeling substance 21a or the attractive modulator 21b. Accordingly, the analyte can be simply detected in the same manner as described above.

In the method (B), as shown in FIGS. 15 and 16, the process of adding the target substance may be performed after the isolation process.

The method of electrochemically detecting an analyte of the present invention further includes a method of electrochemically detecting an electrochemically or photochemically active analyte, comprising: immobilizing an analyte on a solid phase; isolating the solid phase in which the analyte is immobilized; separating the analyte or part of the analyte from the solid phase in which the analyte obtained in the isolation process is immobilized; attracting the separated analyte or part of the analyte to a working electrode in which a trapping substance for trapping the analyte or part of the analyte is not present; and electrochemically detecting the analyte or the part of the analyte [referred to as a method (C)].

According to the method (C), specifically, when the analyte 10 is a nucleic acid, the analyte 10 is first immobilized on the solid phase 31 through the first trapping substance 32 immobilized on the solid phase 31 such as a magnetic bead. Next, components other than the analyte 10 are removed by isolating the solid phase 31 thus obtained. Then, the solid phase 31 in which the complex containing the analyte 10 and the first trapping substance 32 is formed is subjected to heat treatment or restriction enzyme treatment in order to separate the analyte 10 or a part of the analyte 10 (or the labeling substance). Thereafter, the analyte 10 is detected by attracting the target substance to near the working electrode using the attracting liquid and measuring the oxidation reduction current.

[Detection Kit]

The detection kit of the present invention is a detection set for electrochemically detecting an analyte which includes a solid phase in which a first trapping substance for trapping an analyte is immobilized, a label binding substance containing a binding substance for trapping an analyte labeled with a labeling substance, and a test chip which includes a working electrode in which a second trapping substance for trapping a target substance containing a labeling substance which is separated from the binding substance is not present and a counter electrode composed of a conductive material.

The detection kit may further include a separating agent which separates the target substance containing a labeling substance from the solid phase in which the complex containing the labeling substance and the analyte are formed.

The solid phase, the label binding substance, and the test chip are as described above.

The separating agent can be suitably selected depending on the type of the analyte and the first trapping substance. For example, when the analyte is a nucleic acid, a restriction enzyme can be used as the separating agent.

EXAMPLES

Hereinafter, the present invention will be described in detail with reference to Examples, however, the present invention is not limited thereto. In Examples, examples related to the photoelectrochemical detection method of the analyte will be described.

Example 1

It was investigated whether the target substance containing a labeling substance could be attracted to near the working electrode by using differences in polarity.

(1) Preparation of Working Electrode Section

A 200 nm-thick semiconductor layer composed of indium oxide including tin was formed on a substrate composed of silicon dioxide ($SiO_2$) by sputtering and a semiconductor electrode section was obtained. A semiconductor electrode lead for connection to an ammeter was connected to the semiconductor electrode section.

(2) Preparation of Counter Electrode Section

A 200 nm-thick conductive layer composed of a platinum thin film was formed on a substrate composed of silicon dioxide ($SiO_2$) by sputtering and a counter electrode section was obtained. A counter electrode lead for connection to an ammeter was connected to the counter electrode section.

(3) Preparation of Target Substance Containing Labeling Substance

As the target substance containing a labeling substance, a complex composed of DNAs of 24 nucleotide length (attractive modulator) and Alexa 750 (manufactured by Invitrogen) (labeling substance) (the modified labeling substance composed of the labeling substance and the attractive modulator) was used.

(4) Preparation of Attracting Liquid and Electrolytic Solution

It does not need that the attracting liquid for attracting the labeling substance to near the working electrode and the electrolytic solution for using for the electrochemical detection are the same. In the examples, a combination of a liquid which can immobilize and detect with the same liquid (also referred to as an "attracting electrolytic solution") and the target substance containing a labeling substance was used. In the examples, an aprotic polar solvent was used as a solvent to be used for an attracting electrolytic solution.

Acetonitrile and ethylene carbonate were mixed at a volume ratio of 2:3 to prepare an aprotic polar solvent. The aprotic polar solvent was used as the solvent to be used for an attracting electrolyte solution.

Tetrapropylammonium iodide as an electrolyte salt was dissolved in the aprotic polar solvent at a concentration of 0.6

M. Iodine as an electrolyte was dissolved in the obtained solution at concentration of 0.06 M to prepare an attracting electrolytic solution.

(5) Measurement of Photocurrent

Silicone rubber was arranged around the substrate having the working electrode section in which the target substance containing a labeling substance was immobilized so as to have a 0.2 mm-thick side wall.

The concentration of the target substance was adjusted using the electrolytic solution so as to be 0 M (Test No. 1) or 1 nM (Test No. 2) and a detection liquid was obtained. The "detection liquid" means a liquid to be measured when performing the electrochemical detection. The space formed with the silicone rubber was filled with 10 µL of the detection liquid. Then, the space filled with the detection liquid was sealed with the substrate having the counter electrode section from the upper side of the substrate having the working electrode section. Thus, the working electrode section and the counter electrode section were brought into contact with the electrolytic solution. Subsequently, the working electrode lead and the counter electrode lead were connected to the ammeter.

Light from a light source (laser light source with a wavelength of 781 nm and an output power of 13 mW) was emitted from the working electrode section side to the counter electrode section. The labeling substance is excited by photoirradiation, thereby generating electrons. The electrons are transported to the semiconductor layer, and thus an electric current flows between the working electrode section and the counter electrode section. Then, the electric current was measured.

In Test No. 2, a working electrode distinct from the working electrode used in Test No. 1 was used. The working electrode used in Test No. 2 was washed with ethanol and air-dried. Thereafter, the space formed with the silicone rubber was filled with the detection liquid without containing the target substance and the measurement was performed again (Test No. 3).

Figure 17:
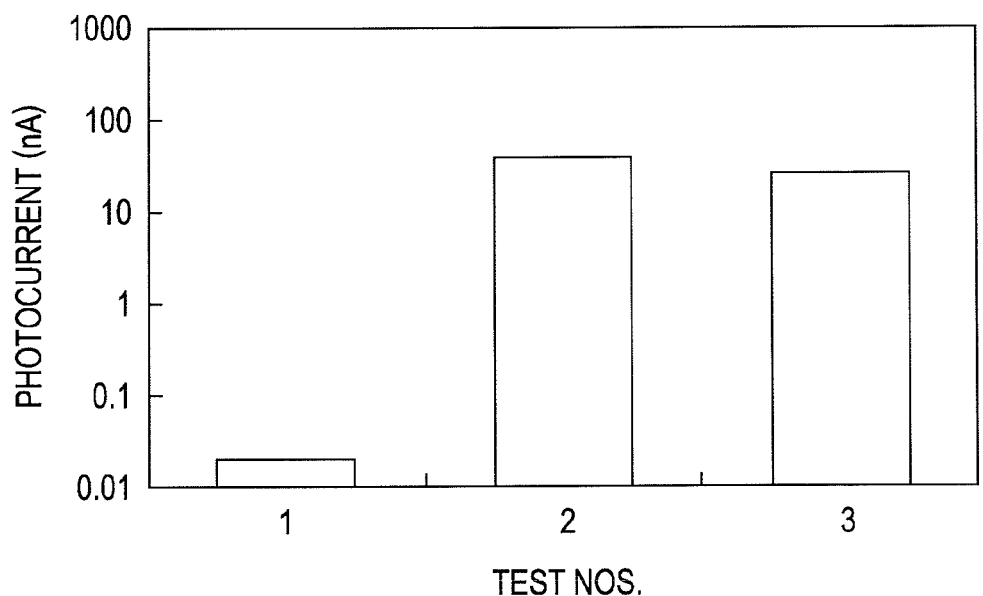
FIG. 17 is a graph showing the measurement results of photocurrent in Test Nos. 1 to 3 in Example 1.

In Example 1, the measurement results of photocurrent in Test Nos. 1 to 3 are shown in FIG. 17.

From the results shown in FIG. 17, it is found that the photocurrent derived from the target substance containing a labeling substance flowed in the detection liquid (Test No. 2) containing the target substance. Therefore, it is suggested that the target substance containing a labeling substance can be detected by using differences in polarity between the modified labeling substance and the attracting electrolytic solution and the working electrode.

From the results shown in FIG. 17, it is found that the photocurrent equal to that of Test No. 2 flowed in the detection liquid (Test No. 3) without containing the target substance. Therefore, it is found that the photocurrent obtained in Test No. 2 is derived from the target substance containing a labeling substance which has been attracted to the working electrode. Further, it is found that the target substance which has been attracted is held on the working electrode even after the replacement of the solution.

Example 2

Water or the protonic polar solvent was used in place of the aprotic polar solvent in Example 1. A liquid prepared by dissolving calcium iodide in water at a concentration of 1.5 M was used as an attracting electrolytic solution containing a chaotropic ion. As the detection liquid, a detection liquid in which the concentration of the target substance was 0 M (Test No. 4) or 1 µM (Test No. 5) was used. Operation was performed in the same manner as described in Example 1 except these points. It was investigated whether the target substance containing a labeling substance could be attracted to near the working electrode by using differences in polarity.

When measuring the photocurrent, in Test No. 5, a working electrode distinct from the working electrode used in Test No. 4 was used. The working electrode used in Test No. 5 was washed with ethanol and air-dried. Thereafter, the space formed with the silicone rubber was filled with the detection liquid without containing the target substance and the measurement was performed again (Test No. 6).

Figure 18:
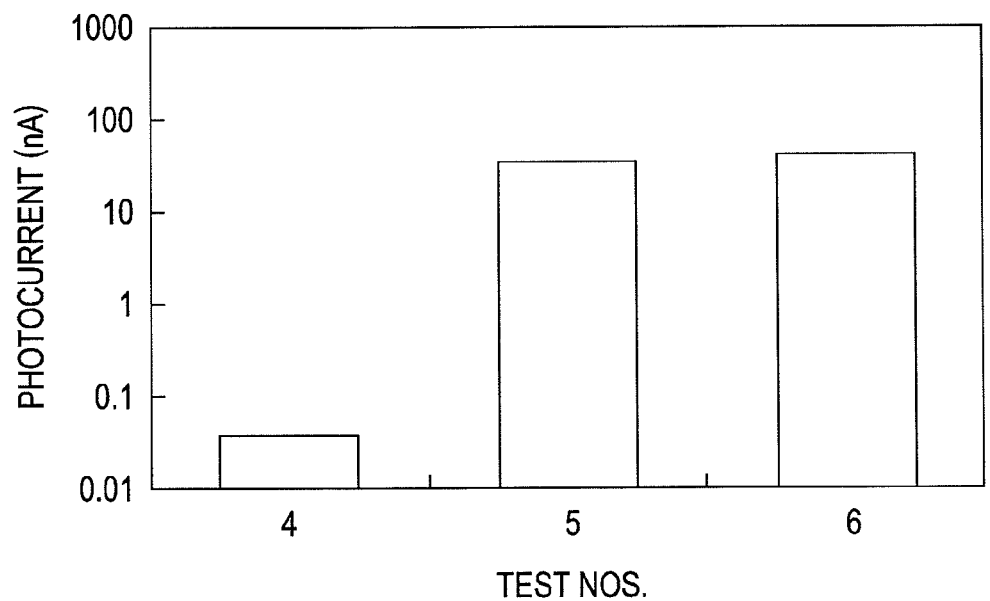
FIG. 18 is a graph showing the measurement results of photocurrent in Test Nos. 4 to 6 in Example 2.

In Example 2, the measurement results of photocurrent in Test Nos. 4 to 6 are shown in FIG. 18.

From the results shown in FIG. 18, it is found that the photocurrent derived from the target substance containing a labeling substance flowed in the detection liquid (Test No. 5) containing the target substance. Therefore, it is suggested that even if the protonic polar solvent was used as a solvent to be used for the attracting electrolytic solution, the target substance can be detected.

From the results shown in FIG. 18, it is found that the photocurrent equal to that of Test No. 5 flowed in the detection liquid (Test No. 6) without containing the target substance. Therefore, it is found that the photocurrent obtained in Test No. 5 is derived from the target substance containing a labeling substance which has been attracted to the working electrode. Further, it is found that the target substance which has been attracted is held on the working electrode even after the replacement of the solution.

Example 3

In this example, Alexa750 (Invitrogen) was used as the target substance containing a labeling substance. As the detection liquid, a detection liquid in which the concentration of the target substance was 0 M (Test No. 7) or 1 µM (Test No. 8) was used. Operation was performed in the same manner as described in Example 1 except these points. It was investigated whether the target substance could be attracted to near the working electrode when the target substance containing a labeling substance was composed only of the labeling substance.

When measuring the photocurrent, in Test No. 8, a working electrode distinct from the working electrode used in Test No. 7 was used. The working electrode used in Test No. 8 was washed with ethanol and air-dried. Thereafter, the space formed with the silicone rubber was filled with the detection liquid without containing the target substance and the measurement was performed again (Test No. 9).

Figure 19:
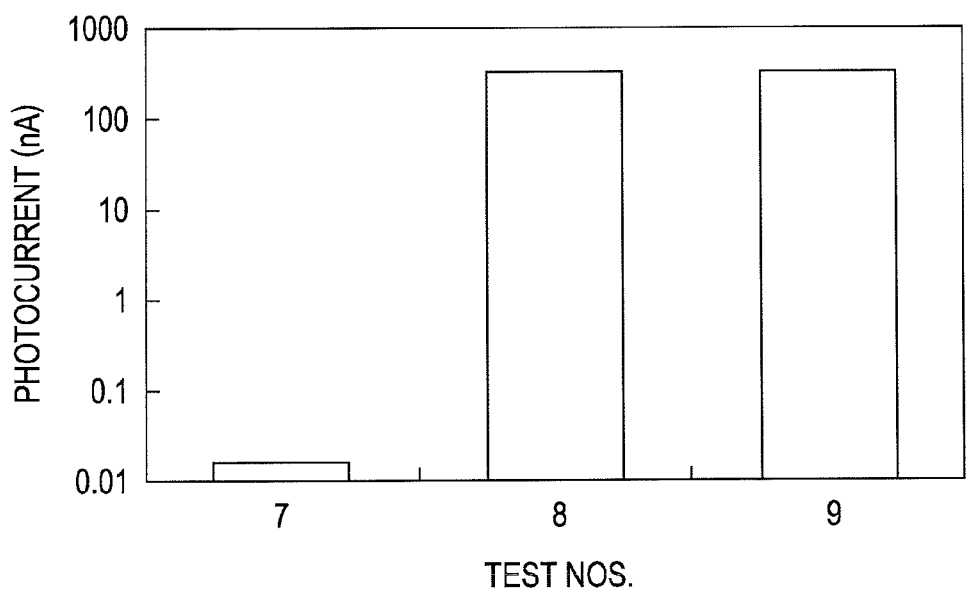
FIG. 19 is a graph showing the measurement results of photocurrent in Test Nos. 7 to 9 in Example 3.

In Example 3, the measurement results of photocurrent in Test Nos. 7 to 9 are shown in FIG. 19.

From the results shown in FIG. 19, it is found that the photocurrent derived from the target substance containing a labeling substance flowed in the detection liquid (Test No. 8) containing the target substance. Therefore, the results suggest that even if only the labeling substance is used as the target substance containing a labeling substance, the target substance can be detected.

From the results shown in FIG. 19, it is found that the photocurrent equal to that of Test No. 8 flowed in the detection liquid (Test No. 9) without containing the target substance. Therefore, it is found that the photocurrent obtained in Test No. 8 is derived from the target substance containing a labeling substance which has been attracted to the working electrode. Further, it is found that the target substance which has been attracted is held on the working electrode even after the replacement of the solution.

In Test No. 2 (FIG. 17), the photocurrent value to the concentration of the target substance is higher than the case of Test No. 8 (FIG. 19). Accordingly, it is found that DNA serves as the attractive modulator which attracts the labeling substance to the working electrode.

Example 4

It was investigated whether the working electrode could be reused by cleaning the working electrode by the simple treatment.

The photocurrent was measured by performing the same operation as Example 1 except that the detection liquid adjusted so that the concentration of the target substance containing a labeling substance in Example 1 was 10 nM was used (Test No. 10: the first time measurement).

As the cleaning treatment for reuse, the working electrode used in Test No. 10 was first washed with ethanol and air-dried. Next, the solution in the space formed with silicone rubber was replaced with a phosphate-buffered saline and a DC voltage (−1V) was applied to the working electrode for 2 minutes. Thereafter, the working electrode was washed with ethanol and air-dried.

After the cleaning treatment, the photocurrent of the detection liquid containing the target substance having a concentration of 0 nM was measured using the working electrode (Test No. 11).

The working electrode used in Test No. 11 was washed with ethanol and air-dried. Thereafter, the photocurrent of the detection liquid containing the target substance having a concentration of 10 nM was measured using the working electrode (Test No. 12: remeasurement).

Figure 20:
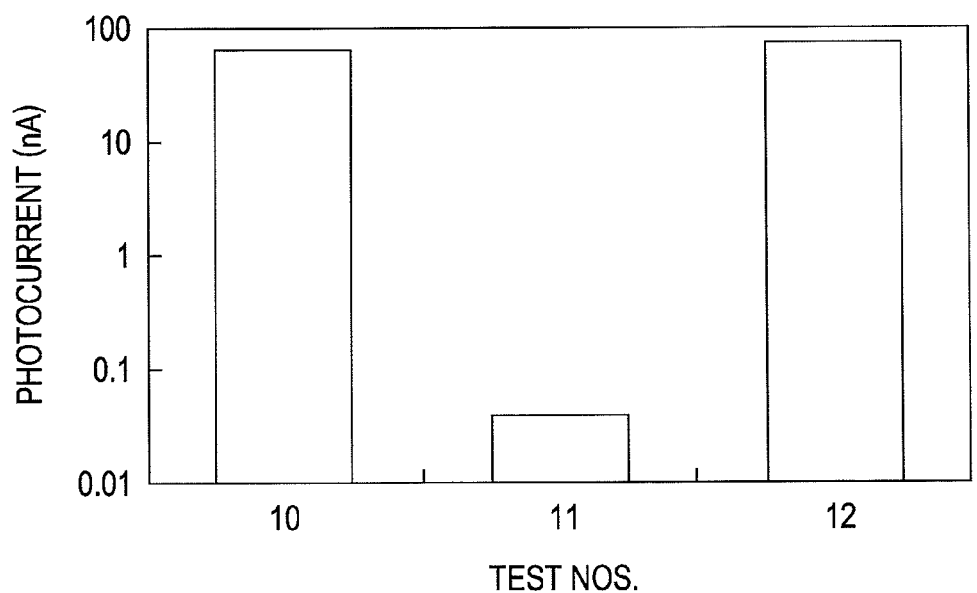
FIG. 20 is a graph showing the measurement results of photocurrent in Test Nos. 10 to 12 in Example 4.

In Example 4, the measurement results of photocurrent in Test Nos. 10 to 12 are shown in FIG. 20.

From the results shown in FIG. 20, it was confirmed that even when the working electrode was cleaned, the photocurrent derived from the target substance containing a labeling substance flowed (Test No. 12). Consequently, it is found that, according to the method of the present invention, the working electrode is reusable.

Example 5

The photocurrent was measured by performing the same operation as Example 1 except that the detection liquid containing the target substance having a concentration of 0 nM (Test No. 13), 0.1 nM (Test No. 14), 1 nM (Test No. 15) or 10 nM (Test No. 16) was measured using the same working electrode subjected to the cleaning treatment for reuse before the measurement was used. The cleaning treatment for reuse was performed in the same manner as the case of Test No. 11 in Example 4.

Figure 21:
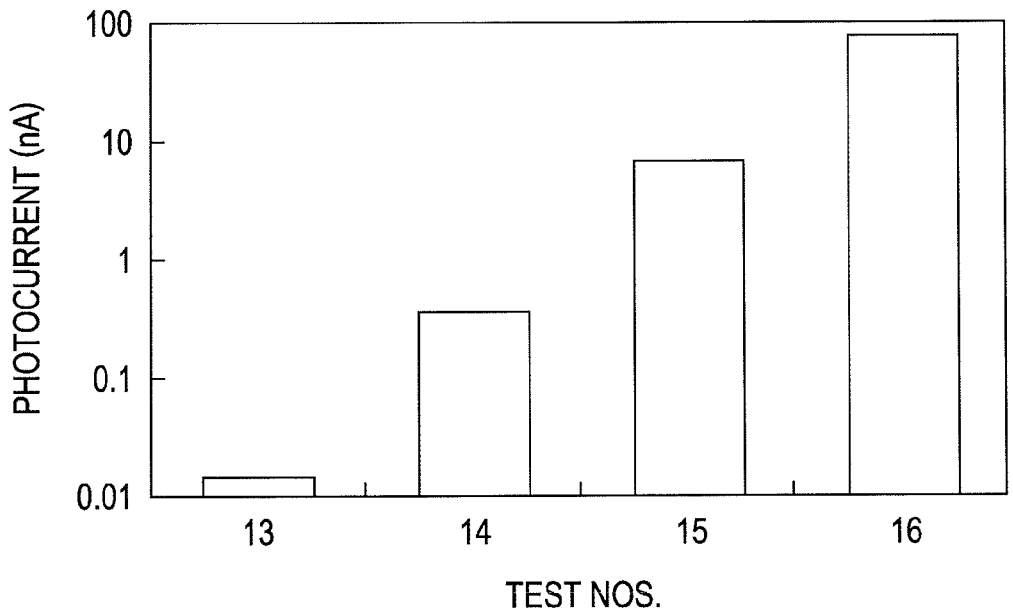
FIG. 21 is a graph showing the measurement results of photocurrent in Test Nos. 13 to 16 in Example 5.

In Example 5, the measurement results of photocurrent in Test Nos. 13 to 16 are shown in FIG. 21.

From the results shown in FIG. 21, it is found that the photocurrent is increased as the concentration of the target substance becomes higher, and thus the target substance containing a labeling substance can be quantified according to the method of the present invention.

Example 6

The surface of the light irradiating section of the working electrode obtained in (1) of Example 1 was subjected to the surface treatment with APTES, i.e., a silane coupling agent.

The photocurrent was measured by performing the same operation as test No. 1 of Example 1 except that the working electrode subjected to the surface treatment with APTES in Example 1 as well as the detection liquid containing the target substance containing a labeling substance with a concentration of 1 nM were used (Test No. 18).

The photocurrent was measured by performing the same operation as described above except that the working electrode which was not subjected to the surface treatment with APTES in the above manner (Test No. 17).

Figure 22:
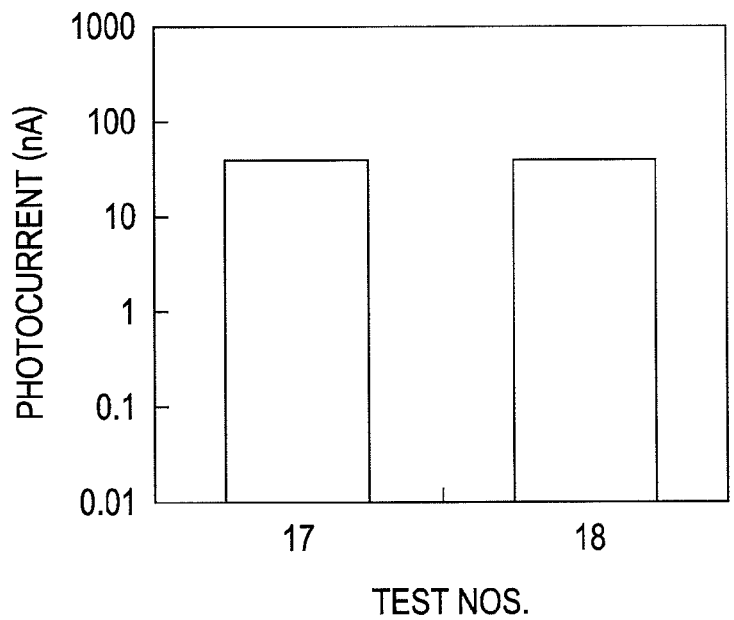
FIG. 22 is a graph showing the measurement results of photocurrent in Test Nos. 17 and 18 in Example 6.

In Example 6, the measurement results of photocurrent in Test Nos. 17 and 18 are shown in FIG. 22.

From the results shown in FIG. 22, it is suggested that even if the working electrode subjected to the surface treatment is used, the photocurrent derived from the target substance containing a labeling substance can be detected.

Example 7

It was investigated whether the target substance could be attracted to near the working electrode when the attracting liquid did not contain a chaotropic ion.

In this example, as the target substance containing a labeling substance, a label binding substance containing a binding substance for trapping the analyte (anti-mouse IgG) labeled with the labeling substance [Alexa 750, manufactured by Invitrogen] was used. As the solvent of the attracting liquid, a mixture of a protic solvent not containing a chaotropic ion and an aprotic solvent [a mixture of a tris buffer saline solution (TBS), acetonitrile (AN), and ethylene carbonate (EC), (a volume ratio of TBS, AN, and EC was 5:2:3)] was used. As the solvent to be used for the electrolytic solution, an aprotic solvent [a mixture with a volume ratio of (acetonitrile and ethylene carbonate) 2:3] was used. Tetrapropylammonium iodide as an electrolyte salt was dissolved in the aprotic polar solvent at a concentration of 0.6 M. Iodine as an electrolyte was dissolved in the obtained solution at concentration of 0.06 M to prepare an electrolytic solution was obtained.

Silicone rubber was arranged around the substrate having the working electrode section obtained in (1) of Example 1 so as to have a 0.2 mm-thick side wall. 10 μL of the attracting liquid in which the concentration of the target substance containing a labeling substance was 0 g/mL (Test No. 19) or 1 μg/mL (Test No. 20) was charged into the space formed with silicone rubber. The space filled with the attracting liquid was sealed with a cover glass from the upper side of the substrate having the working electrode section, followed by being left at rest for 10 minutes. Thereafter, the cover glass and the silicone rubber were removed. The working electrode was washed with ethanol and air-dried (the attracting process).

Then, the silicone rubber was arranged around the substrate having the working electrode section so as to have a 0.2 mm-thick side wall. 10 μL of the electrolytic solution was charged into the space formed with the silicone rubber. Then, the space filled with the electrolytic solution was sealed with the substrate having the counter electrode section obtained in (2) of Example 1 from the upper side of the substrate having the working electrode section. Thus, the working electrode section and the counter electrode section were brought into contact with the electrolytic solution. Subsequently, the working electrode lead and the counter electrode lead were connected to the ammeter.

Light from a light source (laser light source with a wavelength of 781 nm and an output power of 13 mW) was emitted from the working electrode section side to the counter electrode section. Thus, the labeling substance is excited, electrons generated from the excited labeling substance are transported to the semiconductor layer, and the electric current flows between the working electrode section and the counter electrode section. Then, the electric current was measured.

Figure 23:
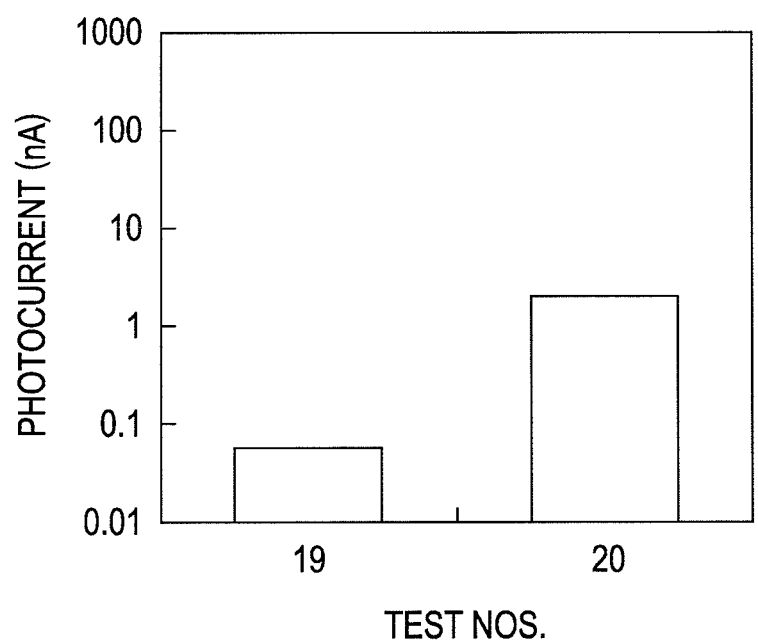
FIG. 23 is a graph showing the measurement results of photocurrent in Test Nos. 19 and 20 in Example 7.

In Example 7, the measurement results of photocurrent in Test Nos. 19 and 20 are shown in FIG. 23.

From the results shown in FIG. 23, it is found that the photocurrent derived from the target substance containing a labeling substance flowed in Test No. 20. Therefore, it is suggested that even if the attracting liquid does not contain a chaotropic ion, the target substance containing a labeling substance can be detected.

In this example, the solution was replaced with the detection liquid without containing the target substance after the attracting process and the photocurrent derived from the target substance was detected. Therefore, it is found that the photocurrent obtained in Test No. 20 is derived from the target substance containing a labeling substance which has been attracted to the working electrode. Further, it is found that the target substance which has been attracted is held on the working electrode even after the replacement of the solution.

Example 8

In this example, it was investigated whether the analyte could be quantified by "the method of electrochemically detecting an analyte" (method (B)) comprising: forming a complex containing a labeling substance and an analyte on a solid phase; isolating the solid phase in which the complex is formed; separating a target substance containing a labeling substance from the complex formed on the solid phase which is obtained in the isolation process.

(1) Analyte

In this example, mouse IgG (manufactured by Sigma) was used as an analyte.

(2) Preparation of Solid Phase with Trapping Substance Modified

Anti-mouse IgG (manufactured by Cappel) was used as the trapping substance and beads (diameter of affinity beads: 5 μm, manufactured by Sumitomo Bakelite Co., Ltd.) in which an amino group was modified as the solid phase were used. 37 mg of the beads was mixed with 1 mL of a buffer for immobilizing proteins (manufactured by Sumitomo Bakelite Co., Ltd.). The mixture was adjusted so that the concentration of anti-mouse IgG was 100 μg/ml, followed by stirring at 37° C. for 4 hours. Subsequently, the supernatant was removed by centrifugal operation and the mixture was washed with PBS. Thereafter, 1 mL of a buffer for inactivation (manufactured by Sumitomo Bakelite Co., Ltd.) was added thereto and stirred at room temperature for 1 hour. The supernatant was removed by the centrifugal operation and the mixture was washed with PBS. A solid phase with the trapping substance modified was prepared by these procedures.

(3) Preparation of Label Binding Substance

A substance in which Alexa750 (labeling substance, manufactured by Invitrogen) was bound to the same anti-mouse IgG as that used for the trapping substance was used as the label binding substance.

The used working electrode and counter electrode sections other than the above-described ones were the same as those used in Example 1. The attracting liquid and the electrolytic solution used herein were the same as those used in Example 7.

(4) Procedure

The procedure in this example will be described based on FIG. 24.

(a) Process of Trapping Analyte

A Tris buffer (TBST) prepared by mixing with 1% Tween was used as a solvent. By using the solvent, each 500 μL with 0.01 ng/mL (Test No. 21), 0.1 ng/mL (Test No. 22), 1 ng/mL (Test No. 23), and 10 ng/mL (Test No. 24) of mouse IgG (analyte) was prepared. The analyte was trapped on the solid phase by mixing the solutions with the solid phase with the trapping substance modified in a microtube and stirring it at room temperature for 1 hour (see FIG. 24 (A)).

(b) Isolation Process

The solid phase in which the analyte was trapped was isolated by the centrifugal operation and the resultant product was washed with TBST (see FIG. 24 (B)).

(c) Process of Adding Target Substance

The concentration of the label binding substance above described was adjusted to 1 μg/ml using TBST as a solvent. 500 μL of the resultant mixture was added to a microtube, which was mixed and stirred at room temperature for 1 hour. Thereafter, a complex composed of the solid phase, the trapping substance, the analyte, and the label binding substance was isolated by the centrifugal operation (see FIG. 24 (C)).

(d) Separation Process

After washing the complex with TBST by the centrifugal operation, the solvent of TBST was replaced by TBS. The final volume was adjusted to 10 μL. Thereafter, the label binding substance was separated from the complex by heating at 60° C. for 15 minutes. The case where the binding of the analyte to the trapping substance is cut by heating and the case where the binding of the analyte to the binding substance is cut by heating may occur. However, in both cases, the label binding substance is separated. Subsequently, the supernatant was collected by centrifugation (see FIG. 24 (D)).

The following attracting process and detection process were performed by the method described in the Example 7 except that 5 μL of a solution collected was dropped on the working electrode in the space formed with silicone rubber, followed by addition of 5 μL of an attractive solvent (see FIGS. 24 (E) and (F)).

Figure 25:
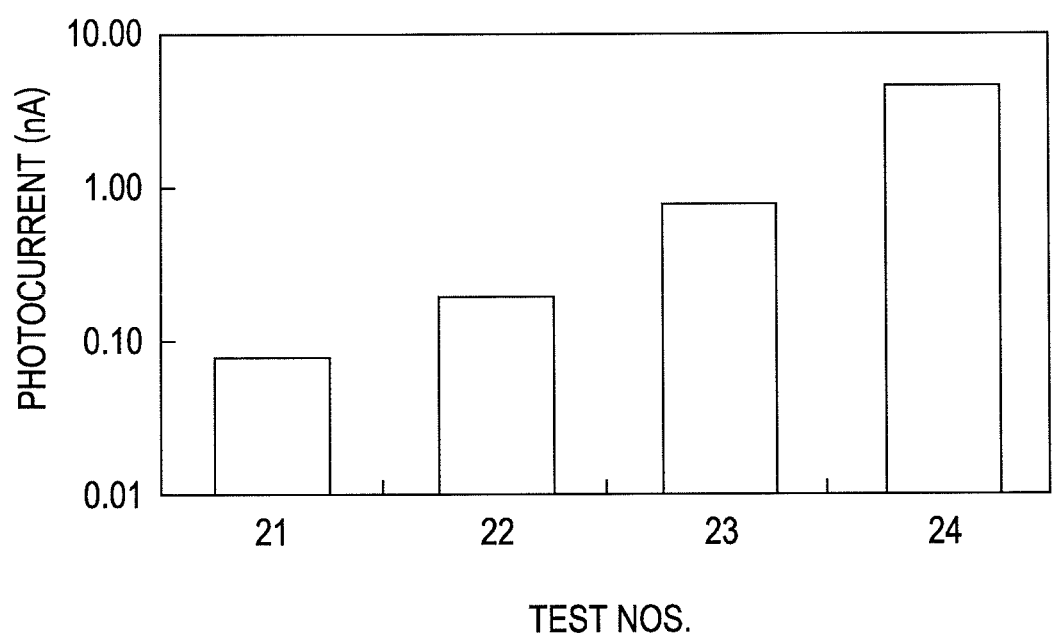
FIG. 25 is a graph showing the measurement results of photocurrent in Test Nos. 21 to 24 in Example 8.

FIG. 25 shows the measurement results of photocurrent in Test Nos. 21 to 24 in Example 8. From the results shown in FIG. 25, it was found that the analyte could be quantified by the method (B) of the present invention because the photocurrent was increased as the concentration of the analyte became higher.

What is claimed is:

1. A method of electrochemically detecting a target substance containing a labeling substance, comprising:
forming a trapped analyte by trapping an analyte on a solid phase containing a trapping substance for trapping the analyte;
adding to the trapped analyte the target substance containing a labeling substance;
attracting the target substance containing a labeling substance in a liquid sample to a working electrode in which the trapping substance for trapping the target substance containing a labeling substance is not present;
immobilizing the target substance containing a labeling substance on the working electrode; and
electrochemically detecting the target substance containing a labeling substance by measuring a photocurrent,
wherein the labeling substance is a photoelectrochemically active substance.

2. The method according to claim 1, wherein the labeling substance is at least one selected from the group consisting of a metal complex, an organic phosphor, a quantum dot, an inorganic phosphor, and a nucleic acid.

3. The method according to claim 1, wherein the target substance containing a labeling substance is a nucleic acid labeled with a labeling substance.

4. The method according to claim 1, wherein the liquid sample contains a chaotropic ion.

5. The method according to claim 4, wherein the chaotropic ion is at least one selected from the group consisting of an iodide ion, a bromide ion, a guanidine ion, a thiocyanic acid ion, a tribromoacetic acid ion, a trichloroacetic acid ion, a perchlorate ion, a dichloroacetic acid ion, a nitrate ion, a chloride ion, an acetate ion, a barium ion, a calcium ion, a lithium ion, a cesium ion, a potassium ion, and a magnesium ion.

6. The method according to claim 1, wherein the liquid sample contains acetonitrile, water or a mixture of acetonitrile and water.

7. The method according to claim 1, wherein the attracting process is a process of attracting the target substance containing a labeling substance to a region where electrons can be transported between the target substance and the working electrode in which the trapping substance is not present or a region where the electronic excitation of a labeling substance occurs by the working electrode in which the trapping substance is not present.

8. The method according to claim 1, wherein the attracting process is a process of attracting the target substance containing a labeling substance to the working electrode by differences in polarity.

9. The method according to claim 1, wherein the attracting process comprises a process of attracting the target substance containing a labeling substance to the working electrode in which the trapping substance is not present by electrophoresis.

10. The method according to claim 1, wherein the detection process is a process of electrochemically detecting the target substance containing a labeling substance in the presence of an electrolytic solution.

11. The method according to claim 10, wherein the electrolytic solution contains acetonitrile ($CH_3CN$), water or a mixture of acetonitrile and water.

12. The method according to claim 1, wherein the working electrode includes a semiconductor.

13. The method according to claim 1, wherein the working electrode contains at least one selected from the group consisting of titanium oxide, zinc oxide, tin oxide, niobium oxide, indium oxide, tungsten oxide, tantalum oxide, and strontium titanate.

14. The method according to claim 13, wherein the working electrode contains indium oxide containing tin or tin oxide containing fluorine.

* * * * *